(12) United States Patent
Cao et al.

(10) Patent No.: US 10,833,217 B2
(45) Date of Patent: Nov. 10, 2020

(54) METHODS OF MAKING SEMICONDUCTOR RADIATION DETECTOR

(71) Applicant: SHENZHEN XPECTVISION TECHNOLOGY CO., LTD., Shenzhen (CN)

(72) Inventors: Peiyan Cao, Shenzhen (CN); Yurun Liu, Shenzhen (CN)

(73) Assignee: SHENZHEN XPECTVISION TECHNOLOGY CO., LTD., Shenzhen (CN)

( * ) Notice: Subject to any disclaimer, the term of this patent is extended or adjusted under 35 U.S.C. 154(b) by 0 days.

(21) Appl. No.: 16/565,458

(22) Filed: Sep. 9, 2019

(65) Prior Publication Data

US 2020/0013919 A1 Jan. 9, 2020

Related U.S. Application Data

(63) Continuation of application No. PCT/CN2017/081400, filed on Apr. 21, 2017.

(51) Int. Cl.
*H01L 21/00* (2006.01)
*H01L 31/18* (2006.01)
(Continued)

(52) U.S. Cl.
CPC .......... *H01L 31/1832* (2013.01); *A61B 6/035* (2013.01); *A61B 6/14* (2013.01);
(Continued)

(58) Field of Classification Search
CPC .......... H01L 31/1832; H01L 27/14634; H01L 27/14636; H01L 31/02002; H01L 31/0224;
(Continued)

(56) References Cited

U.S. PATENT DOCUMENTS

| 5,368,882 | A | * | 11/1994 | Tran | ...................... | H01L 31/115 |
| | | | | | | 427/65 |
| 2004/0149983 | A1 | * | 8/2004 | Lee | ...................... | H03B 15/003 |
| | | | | | | 257/31 |

(Continued)

FOREIGN PATENT DOCUMENTS

WO 2017041221 A1 3/2017

*Primary Examiner* — Richard A Booth
(74) *Attorney, Agent, or Firm* — IPro, PLLC

(57) ABSTRACT

Disclosed herein is an apparatus and a method of making the apparatus. The method comprises obtaining a plurality of semiconductor single crystal chunks. Each of the plurality of semiconductor single crystal chunks may have a first surface and a second surface. The second surface may be opposite to the first surface. The method may further comprise bonding the plurality of semiconductor single crystal chunks by respective first surfaces to a first semiconductor wafer. The plurality of semiconductor single crystal chunks forming a radiation absorption layer. The method may further comprise forming a plurality of electrodes on respective second surfaces of each of the plurality of semiconductor single crystal chunks, depositing pillars on each of the plurality of semiconductor single crystal chunks and bonding the plurality of semiconductor single crystal chunks to a second semiconductor wafer by the pillars.

22 Claims, 24 Drawing Sheets

(51) Int. Cl.
    *A61B 6/03*     (2006.01)
    *A61B 6/14*     (2006.01)
    *G01T 1/24*     (2006.01)
    *H01J 37/244*     (2006.01)
    *H01L 27/146*     (2006.01)
    *H01L 31/02*     (2006.01)
    *H01L 31/0224*     (2006.01)
    *H01L 31/0296*     (2006.01)
    *H01L 31/08*     (2006.01)
    *A61B 6/00*     (2006.01)
    *H01J 37/26*     (2006.01)

(52) U.S. Cl.
    CPC ............ G01T 1/241 (2013.01); H01J 37/244 (2013.01); H01L 27/1469 (2013.01); H01L 27/14634 (2013.01); H01L 27/14636 (2013.01); H01L 27/14676 (2013.01); H01L 27/14696 (2013.01); H01L 31/02002 (2013.01); H01L 31/02016 (2013.01); H01L 31/0224 (2013.01); H01L 31/02966 (2013.01); H01L 31/085 (2013.01); H01L 31/186 (2013.01); *A61B 6/502* (2013.01); *A61B 6/504* (2013.01); *H01J 37/26* (2013.01); *H01J 2237/24475* (2013.01)

(58) Field of Classification Search
    CPC ............. H01L 31/02966; H01L 31/085; H01L 31/186; A61B 6/035; A61B 6/14; G01T 1/241; H01J 37/244
    See application file for complete search history.

(56) References Cited

U.S. PATENT DOCUMENTS

| | | |
|---|---|---|
| 2010/0244287 A1 | 9/2010 | Hsu et al. |
| 2015/0243825 A1* | 8/2015 | Keasler ............... H01L 31/1013 257/184 |
| 2015/0276945 A1 | 10/2015 | Spartiotis et al. |

* cited by examiner

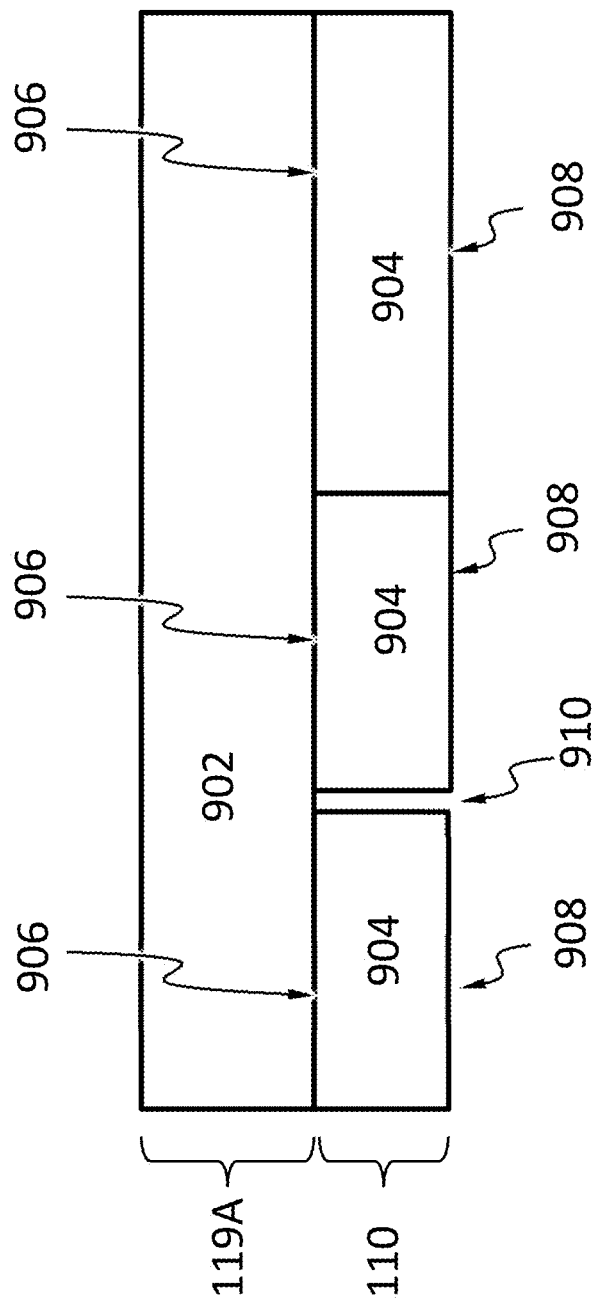

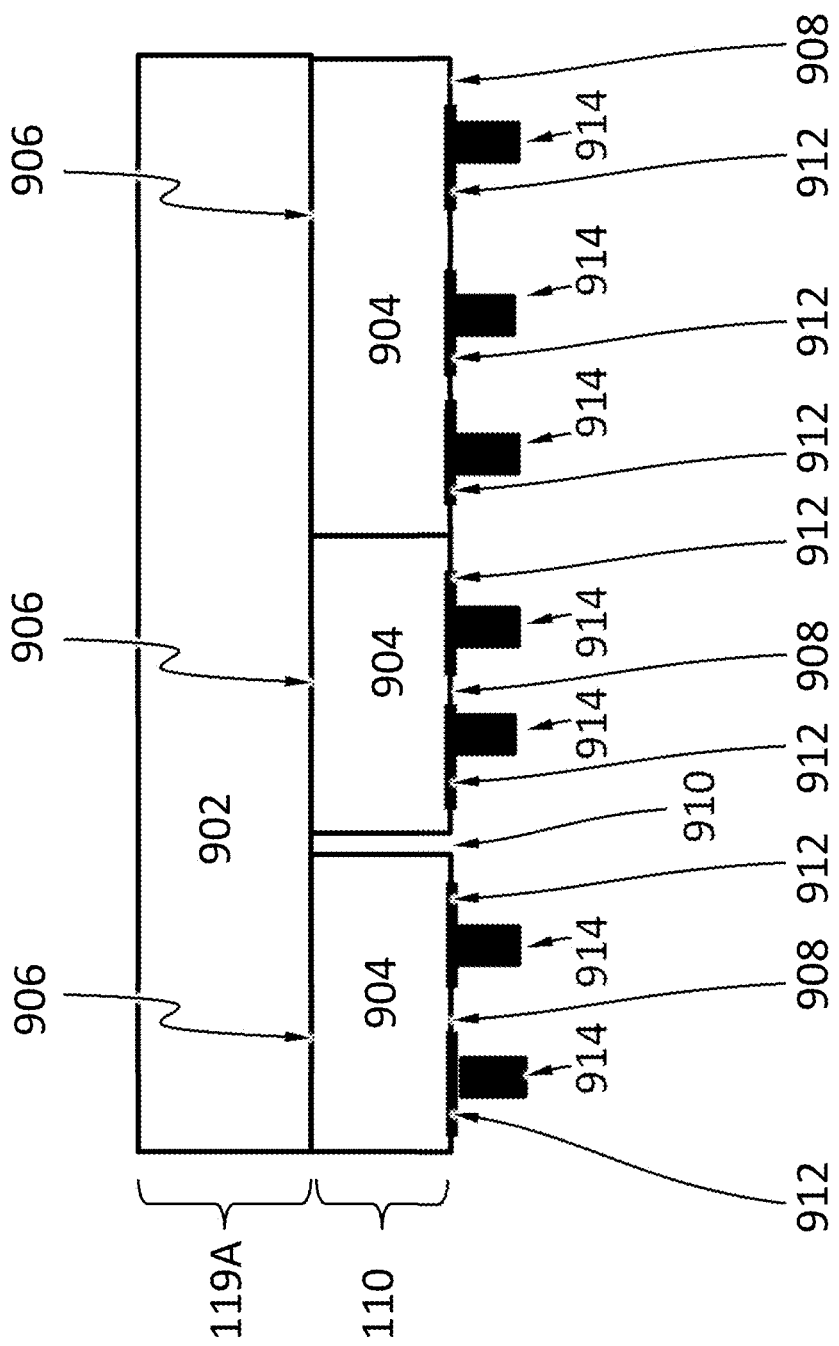

METHODS OF MAKING SEMICONDUCTOR RADIATION DETECTOR

TECHNICAL FIELD

The disclosure herein relates to radiation detectors, particularly relates to methods of making semiconductor radiation detectors.

BACKGROUND

A radiation detector is a device that measures a property of a radiation. Examples of the property may include a spatial distribution of the intensity, phase, and polarization of the radiation. The radiation may be one that has interacted with a subject. For example, the radiation measured by the radiation detector may be a radiation that has penetrated or reflected from the subject. The radiation may be an electromagnetic radiation such as infrared light, visible light, ultraviolet light, X-ray or γ-ray. The radiation may be of other types such as α-rays and β-rays.

One type of radiation detectors is based on interaction between the radiation and a semiconductor. For example, a radiation detector of this type may have a semiconductor layer that absorbs the radiation and generate charge carriers (e.g., electrons and holes) and circuitry for detecting the charge carriers.

SUMMARY

Disclosed herein is a method of making an apparatus suitable for detecting radiation, the method may comprises: obtaining a plurality of semiconductor single crystal chunks each having a first surface and a second surface, the second surface being opposite to the first surface; bonding the plurality of semiconductor single crystal chunks by respective first surfaces to a first semiconductor wafer, the plurality of semiconductor single crystal chunks forming a radiation absorption layer; forming a plurality of electrodes on respective second surfaces of each of the plurality of semiconductor single crystal chunks; depositing pillars on each of the plurality of semiconductor single crystal chunks; and bonding the plurality of semiconductor single crystal chunks to a second semiconductor wafer by the pillars.

According to an embodiment, the plurality of semiconductor single crystal chunks are cadmium zinc telluride (CdZnTe) chunks.

According to an embodiment, the plurality of semiconductor single crystal chunks are bonded to the first semiconductor wafer by glue or plastic molding.

According to an embodiment, the first semiconductor wafer is conductive and serve as a common electrode for the plurality of semiconductor single crystals chunks.

According to an embodiment, the plurality of electrodes on the plurality of semiconductor single crystal chunks are formed by semiconductor wafer processes.

According to an embodiment, the pillars are conductive pillar bumps.

According to an embodiment, the pillars are deposited using semiconductor wafer processes.

According to an embodiment, the method may further comprises polishing the second surfaces of the plurality of semiconductor single crystal chunks so that the plurality of semiconductor single crystal chunks are of the same thickness.

According to an embodiment, the first semiconductor wafer forms a common electrode for the plurality of semiconductor single crystal chunks.

According to an embodiment, the plurality of semiconductor single crystal chunks form resistors between the common electrode at the first surfaces and the plurality of electrodes on the second surfaces.

According to an embodiment, the radiation absorption layer is configured to detect one of electromagnetic radiation including ultraviolet (UV), X-ray, gamma ray.

According to an embodiment, the radiation absorption layer is configured to detect one of particle radiation including alpha particles, beta particles and neutron particles.

According to an embodiment, bonding of the plurality of semiconductor single crystal chunks to the second semiconductor wafer is performed by wafer level room temperature bonding.

According to an embodiment, the second semiconductor wafer comprises an electronics layer for processing signals generated in the radiation absorption layer.

According to an embodiment, the electronics layer comprises an electronics system connected to one of the plurality of electrodes of the plurality of semiconductor single crystal chunks, the electronics system comprises: a first voltage comparator configured to compare a voltage of at least one of the electrodes to a first threshold; a second voltage comparator configured to compare the voltage to a second threshold; a counter configured to register a number of radiation photons or particles reaching the radiation absorption layer; a controller; wherein the controller is configured to start a time delay from a time at which the first voltage comparator determines that an absolute value of the voltage equals or exceeds an absolute value of the first threshold; wherein the controller is configured to activate the second voltage comparator during the time delay; wherein the controller is configured to cause the number registered by the counter to increase by one, if the second voltage comparator determines that an absolute value of the voltage equals or exceeds an absolute value of the second threshold.

According to an embodiment, the electronics system further comprises a capacitor module electrically connected to the electrode, and the capacitor module is configured to collect charge carriers from the electrode.

According to an embodiment, the controller is configured to activate the second voltage comparator at a beginning or expiration of the time delay.

According to an embodiment, the electronics system further comprises a voltmeter, wherein the controller is configured to cause the voltmeter to measure the voltage upon expiration of the time delay.

According to an embodiment, the controller is configured to determine a radiation particle energy based on a value of the voltage measured upon expiration of the time delay.

According to an embodiment, the controller is configured to connect the electrode to an electrical ground.

According to an embodiment, a rate of change of the voltage is substantially zero at expiration of the time delay.

According to an embodiment, a rate of change of the voltage is substantially non-zero at expiration of the time delay.

Disclosed herein is an apparatus for detecting radiation. The apparatus may comprise a radiation absorption layer that may comprises a first semiconductor wafer, a second semiconductor wafer and a plurality of semiconductor single crystal chunks. Each of the plurality of semiconductor single crystal chunks may have a first surface and a second surface with the second surface being opposite to the first surface.

The plurality of semiconductor single crystal chunks may have different sizes and gaps in between, and may be bonded by respective first surfaces to the first semiconductor wafer. A plurality of electrodes may be formed on respective second surfaces of each of the plurality of semiconductor single crystal chunks and the plurality of semiconductor single crystal chunks may be bonded to the second semiconductor wafer by pillars.

According to an embodiment, the plurality of semiconductor single crystal chunks are cadmium zinc telluride (CdZnTe) chunks.

Disclosed herein is a system comprising the apparatus disclosed herein and a radiation source, wherein the system is configured to perform radiography on human chest or abdomen.

Disclosed herein is a system comprising the apparatus disclosed herein and a radiation source, wherein the system is configured to perform radiography on human mouth.

Disclosed herein is a cargo scanning or non-intrusive inspection (NII) system, comprising the apparatus disclosed herein and a radiation source, wherein the cargo scanning or non-intrusive inspection (NII) system is configured to form an image using backscattered radiation.

Disclosed herein is a cargo scanning or non-intrusive inspection (NII) system, comprising the apparatus disclosed herein and a radiation source, wherein the cargo scanning or non-intrusive inspection (NII) system is configured to form an image using radiation transmitted through an object inspected.

Disclosed herein is a full-body scanner system comprising the apparatus disclosed herein and a radiation source.

Disclosed herein is a computed tomography (CT) system comprising the apparatus disclosed herein and a radiation source.

Disclosed herein is an electron microscope comprising the apparatus disclosed herein, an electron source and an electronic optical system.

Disclosed herein is a system comprising the apparatus disclosed herein, wherein the system is an X-ray telescope, or an X-ray microscopy, or wherein the system is configured to perform mammography, industrial defect detection, microradiography, casting inspection, weld inspection, or digital subtraction angiography.

BRIEF DESCRIPTION OF FIGURES

FIG. 10A schematically shows a cross-sectional view of a semiconductor wafer and a plurality of semiconductor single crystal chunks bonded thereon, according to an embodiment.

FIG. 10C schematically shows pillars deposited on the plurality of semiconductor single crystal chunks of FIG. 10B, according to an embodiment.

DETAILED DESCRIPTION

Figure 1A:
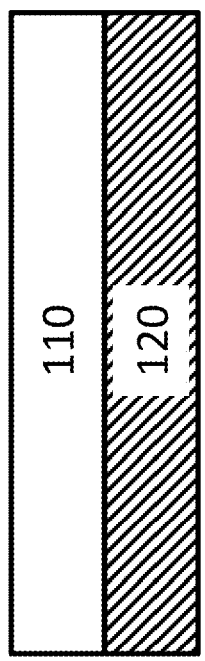
FIG. 1A schematically shows a radiation detector, according to an embodiment.

FIG. 1A schematically shows a cross-sectional view of a radiation detector 100, according to an embodiment. The detector 100 may include a radiation absorption layer 110 and an electronics layer 120 (e.g., an ASIC) for processing or analyzing electrical signals incident radiation generates in the radiation absorption layer 110. In an embodiment, the detector 100 does not comprise a scintillator. The radiation absorption layer 110 may include a semiconductor material such as, silicon, germanium, GaAs, CdTe, CdZnTe, or a combination thereof. The semiconductor may have a high mass attenuation coefficient for the radiation energy of interest. In some embodiments, the radiation may be an electromagnetic radiation such as infrared light, visible light, ultraviolet light, X-ray or γ-ray, and the radiation particles may be photons. In some other embodiments, the radiation may be charged particles such as a and β particles or non-charged particles such as neutrons. In some portions of the description, X-ray is used as an example for various types of radiation described herein.

Figure 1B:
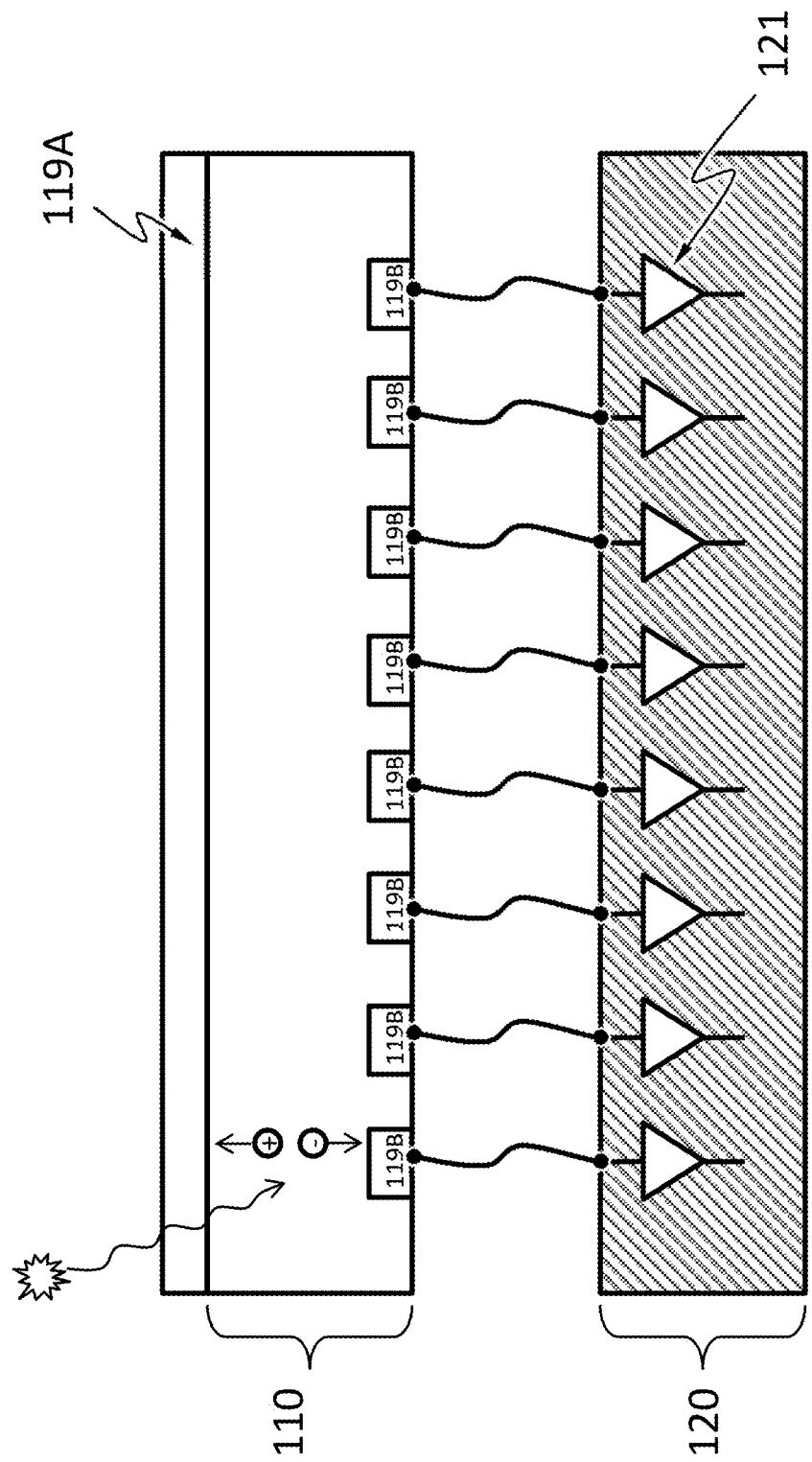
FIG. 1B shows a radiation detector, according an embodiment.

As shown in a detailed cross-sectional view of the detector 100 in FIG. 1B, according to an embodiment, the radiation absorption layer 110 may include a resistor of a semiconductor material such as, silicon, germanium, GaAs, CdTe, CdZnTe, or a combination thereof, but does not include a diode.

When radiation particle hits the radiation absorption layer 110 including a resistor, it may be absorbed and generate one or more charge carriers by a number of mechanisms. A radiation particle may generate 10 to 100000 charge carriers. The charge carriers may drift to the electrical contacts 119A and 119B under an electric field. The field may be an external electric field. The electrical contact 119B includes discrete portions. In an embodiment, the charge carriers may drift in directions such that the charge carriers generated by a single radiation particle are not substantially shared by two different discrete portions of the electrical contact 119B ("not substantially shared" here means less than 5%, less than 2% or less than 1% of these charge carriers flow to a different one of the discrete portions than the rest of the charge carriers). In an embodiment, the charge carriers generated by a single radiation particle can be shared by two different discrete portions of the electrical contact 119B. Charge carriers generated by a radiation particle incident around the footprint of one of these discrete portions of the electrical contact 119B are not substantially shared with another of these discrete portions of the electrical contact 119B. The area around a discrete portion of the electrical contact 119B in which substantially all (more than 95%, more than 98% or more than 99% of) charge carriers generated by a radiation particle incident therein flow to the discrete portion of the electrical contact 119B is called a pixel associated with the discrete portion of the electrical contact 119B. Namely, less than 5%, less than 2% or less than 1% of these charge carriers flow beyond the pixel associated with the one discrete portion of the electrical contact 119B. By measuring the drift current flowing into each of the discrete portion of the electrical contact 119B, or the rate of change of the voltage of each of the discrete portions of the electrical contact 119B, the number of radiation particles absorbed (which relates to the incident radiation intensity) and/or the energies thereof in the pixels associated with the discrete portions of the electrical contact 119B may be determined. Thus, the spatial distribution (e.g., an image) of incident radiation intensity may be determined by individually measuring the drift current into each one of an array of discrete portions of the electrical contact 119B or measuring the rate of change of the voltage of each one of an array of discrete portions of the electrical contact 119B. The pixels may be organized in any suitable array, such as, a square array, a triangular array and a honeycomb array. The pixels may have any suitable shape, such as, circular, triangular, square, rectangular, and hexangular. The pixels may be individually addressable.

The electronics layer 120 may include an electronics system 121 suitable for processing or interpreting signals generated by radiation particles incident on the radiation absorption layer 110. The electronics system 121 may include an analog circuitry such as a filter network, amplifiers, integrators, and comparators, or a digital circuitry such as a microprocessors, and memory. The electronics system 121 may include components shared by the pixels or components dedicated to a single pixel. For example, the electronics system 121 may include an amplifier dedicated to each pixel and a microprocessor shared among all the pixels.

Figure 2:
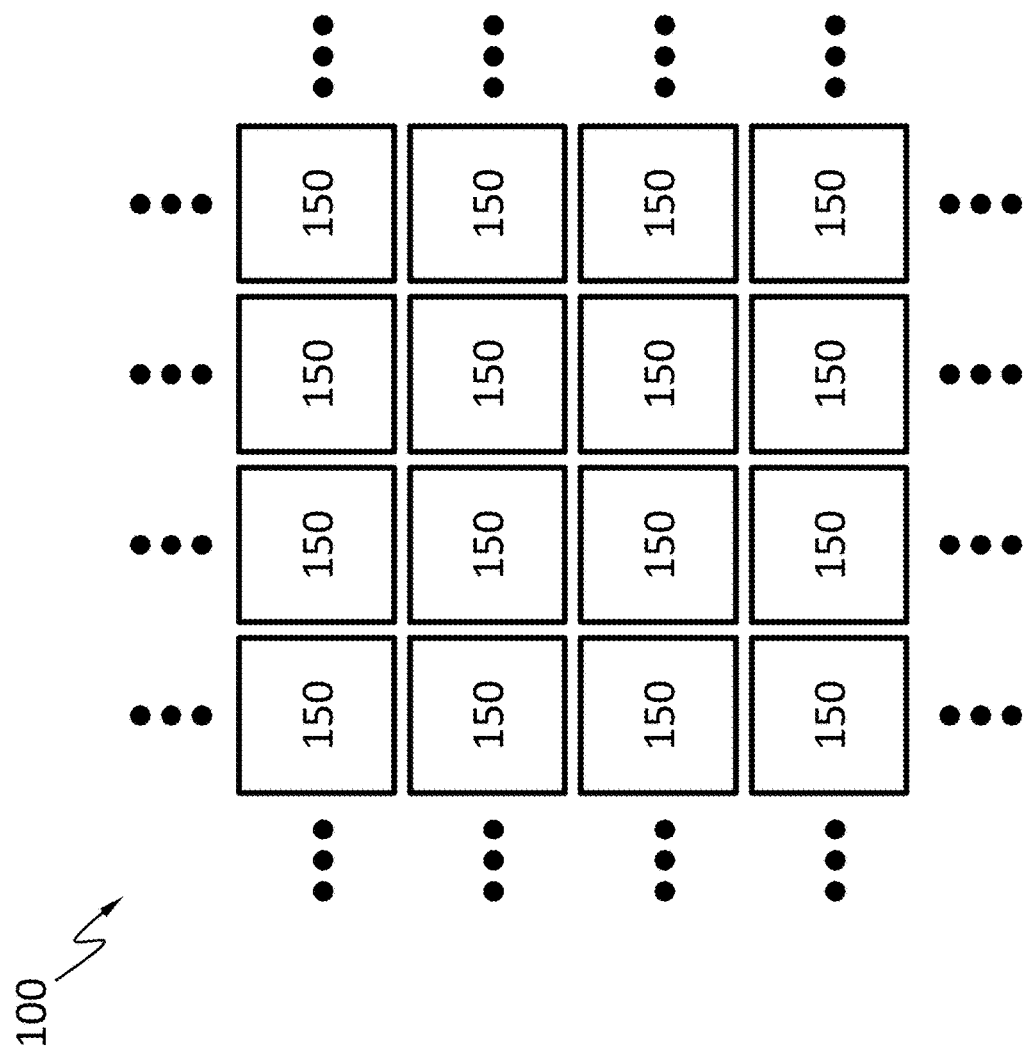
FIG. 2 shows an exemplary top view of a portion of the detector in FIG. 1A, according to an embodiment.

FIG. 2 schematically shows that the detector 100 may have an array of pixels 150. The array may be a rectangular array, a honeycomb array, a hexagonal array or any other suitable array. Each pixel 150 may be configured to detect a radiation particle incident thereon, measure the energy of the radiation particle, or both. For example, each pixel 150 may be configured to count numbers of radiation particles incident thereon whose energy falls in a plurality of bins, within a period of time. All the pixels 150 may be configured to count the numbers of radiation particles incident thereon within a plurality of bins of energy within the same period of time. Each pixel 150 may have its own analog-to-digital converter (ADC) configured to digitize an analog signal representing the energy of an incident radiation particle into a digital signal. The ADC may have a resolution of 10 bits or higher. Each pixel 150 may be configured to measure its dark current, such as before or concurrently with each radiation particle incident thereon. Each pixel 150 may be configured to deduct the contribution of the dark current from the energy of the radiation particle photon incident thereon. The pixels 150 may be configured to operate in parallel. For example, when one pixel 150 measures an incident radiation particle, another pixel 150 may be waiting for a radiation particle to arrive. The pixels 150 may be but do not have to be individually addressable.

Figure 3A:
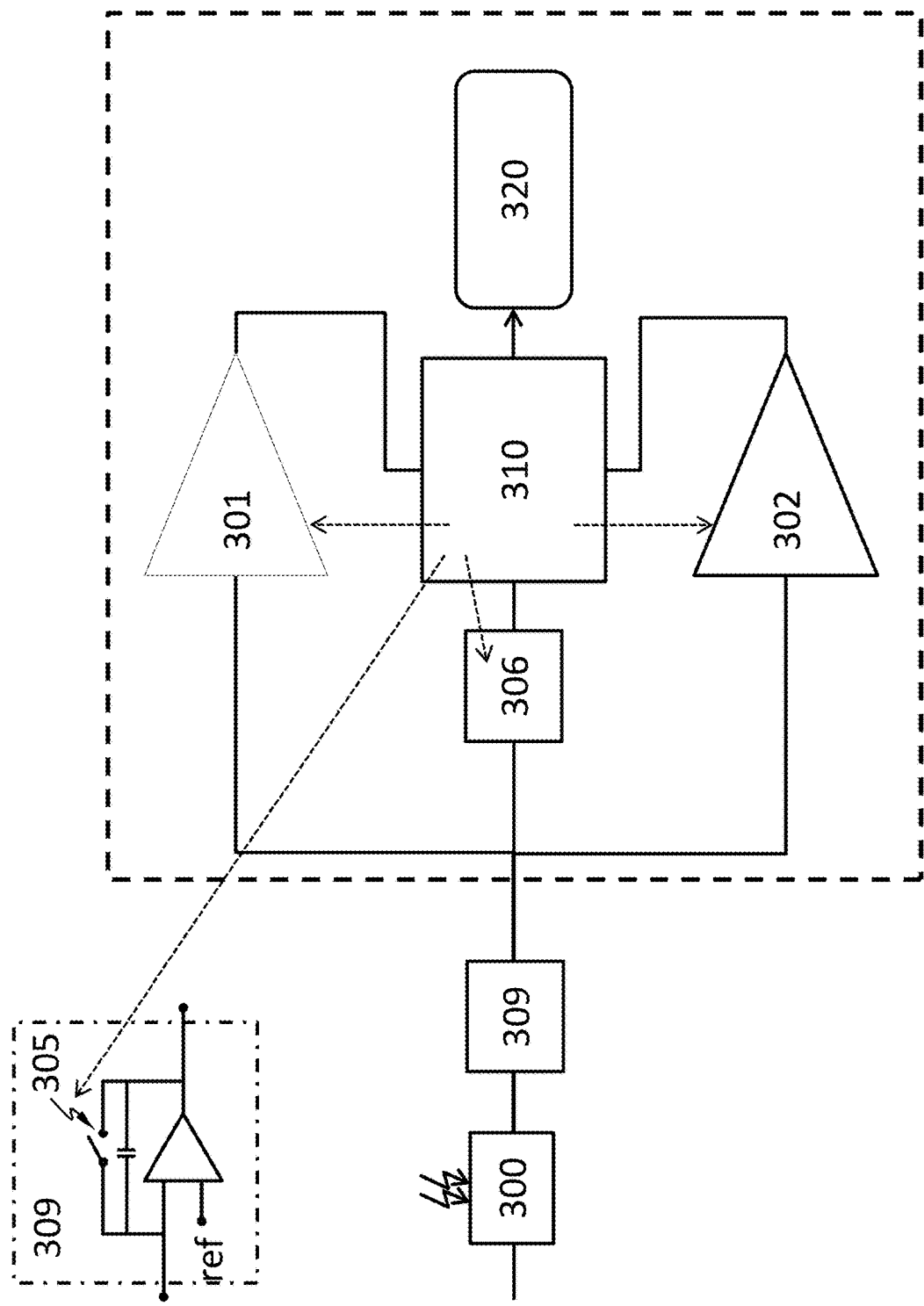
FIG. 3A and FIG. 3B each show a component diagram of an electronics system of the detector in FIG. 1A and FIG. 1B, according to an embodiment.
Figure 3B:
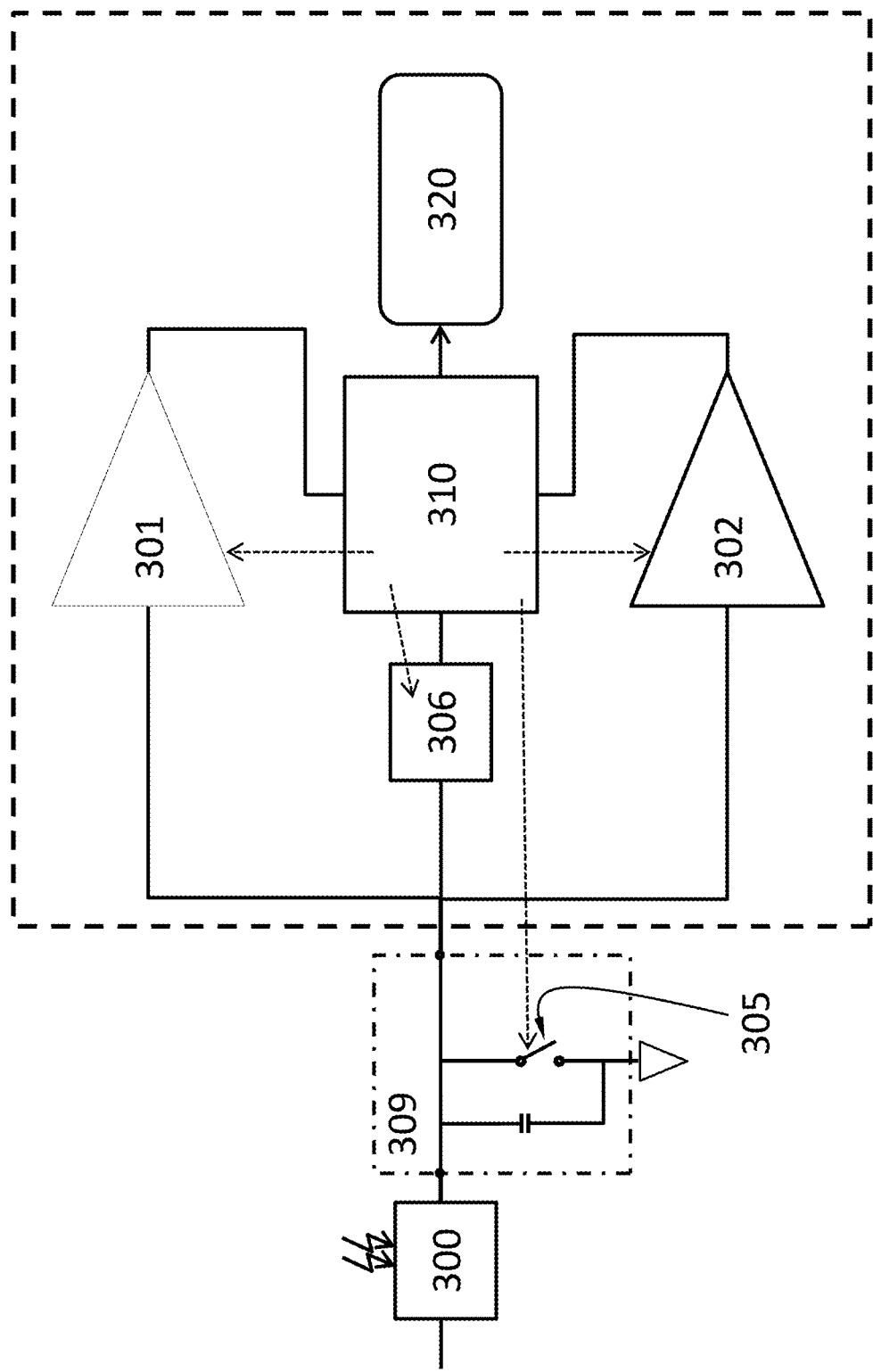

FIG. 3A and FIG. 3B each show a component diagram of the electronics system 121, according to an embodiment. The electronics system 121 may include a first voltage comparator 301, a second voltage comparator 302, a counter 320, a switch 305, a voltmeter 306 and a controller 310.

The first voltage comparator 301 is configured to compare the voltage of an electrode or electrical contact of a resistor 300 to a first threshold. The resistor 300 may be formed by semiconductor material in the absorption layer 110. Alternatively, the first voltage comparator 301 is configured to compare the voltage of an electrical contact (e.g., a discrete portion of electrical contact 119B) to a first threshold. The first voltage comparator 301 may be configured to monitor the voltage directly, or calculate the voltage by integrating an electric current flowing through the resistor or electrical contact over a period of time. The first voltage comparator 301 may be controllably activated or deactivated by the controller 310. The first voltage comparator 301 may be a continuous comparator. Namely, the first voltage comparator 301 may be configured to be activated continuously, and monitor the voltage continuously. The first voltage comparator 301 configured as a continuous comparator reduces the chance that the system 121 misses signals generated by an incident radiation particle. The first voltage comparator 301 configured as a continuous comparator is especially suitable when the incident radiation intensity is relatively high. The first voltage comparator 301 may be a clocked comparator, which has the benefit of lower power consumption. The first voltage comparator 301 configured as a clocked comparator may cause the system 121 to miss signals generated by some incident radiation particles. When the incident radiation intensity is low, the chance of missing an incident radiation particle is low because the time interval between two successive photons is relatively long. Therefore, the first voltage comparator 301 configured as a clocked comparator is especially suitable when the incident radiation intensity is relatively low. The first threshold may be 5-10%, 10%-20%, 20-30%, 30-40% or 40-50% of the maximum voltage one incident radiation particle may generate in the resistor. The maximum voltage may depend on the energy of the incident radiation particle (e.g., the wavelength of the incident X-ray), the material of the radiation absorption layer 110, and other factors. For example, the first threshold may be 50 mV, 100 mV, 150 mV, or 200 mV.

The second voltage comparator 302 is configured to compare the voltage to a second threshold. The second voltage comparator 302 may be configured to monitor the voltage directly, or calculate the voltage by integrating an electric current flowing through the resistor or the electrical contact over a period of time. The second voltage comparator 302 may be a continuous comparator. The second voltage comparator 302 may be controllably activate or deactivated by the controller 310. When the second voltage comparator 302 is deactivated, the power consumption of the second voltage comparator 302 may be less than 1%, less than 5%, less than 10% or less than 20% of the power consumption when the second voltage comparator 302 is activated. The absolute value of the second threshold is greater than the absolute value of the first threshold. As used herein, the term "absolute value" or "modulus" |x| of a real number x is the non-negative value of x without regard to its sign. Namely, $$|x| = \begin{cases} x, \text{ if } x \geq 0 \\ -x, \text{ if } x \leq 0 \end{cases}.$$

The second threshold may be 200%-300% of the first threshold. The second threshold may be at least 50% of the maximum voltage one incident radiation particle may generate in the resistor. For example, the second threshold may be 100 mV, 150 mV, 200 mV, 250 mV or 300 mV. The second voltage comparator 302 and the first voltage comparator 301 may be the same component. Namely, the system 121 may have one voltage comparator that can compare a voltage with two different thresholds at different times.

The first voltage comparator 301 or the second voltage comparator 302 may include one or more op-amps or any other suitable circuitry. The first voltage comparator 301 or the second voltage comparator 302 may have a high speed to allow the system 121 to operate under a high flux of incident radiation. However, having a high speed is often at the cost of power consumption.

The counter 320 is configured to register a number of radiation particles reaching the resistor. The counter 320 may be a software component (e.g., a number stored in a computer memory) or a hardware component (e.g., a 4017 IC and a 7490 IC).

The controller 310 may be a hardware component such as a microcontroller and a microprocessor. The controller 310 is configured to start a time delay from a time at which the first voltage comparator 301 determines that the absolute value of the voltage equals or exceeds the absolute value of the first threshold (e.g., the absolute value of the voltage increases from below the absolute value of the first threshold to a value equal to or above the absolute value of the first threshold). The absolute value is used here because the voltage may be negative or positive, depending on which side of the resistor's electrical contact is used. The controller 310 may be configured to keep deactivated the second voltage comparator 302, the counter 320 and any other circuits the operation of the first voltage comparator 301 does not require, before the time at which the first voltage comparator 301 determines that the absolute value of the voltage equals or exceeds the absolute value of the first threshold. The time delay may expire before or after the voltage becomes stable, i.e., the rate of change of the voltage is substantially zero. The phase "the rate of change of the voltage is substantially zero" means that temporal change of the voltage is less than 0.1%/ns. The phase "the rate of change of the voltage is substantially non-zero" means that temporal change of the voltage is at least 0.1%/ns.

The controller 310 may be configured to activate the second voltage comparator during (including the beginning and the expiration) the time delay. In an embodiment, the controller 310 is configured to activate the second voltage comparator at the beginning of the time delay. The term "activate" means causing the component to enter an operational state (e.g., by sending a signal such as a voltage pulse or a logic level, by providing power, etc.). The term "deactivate" means causing the component to enter a non-operational state (e.g., by sending a signal such as a voltage pulse or a logic level, by cut off power, etc.). The operational state may have higher power consumption (e.g., 10 times higher, 100 times higher, 1000 times higher) than the non-operational state. The controller 310 itself may be deactivated until the output of the first voltage comparator 301 activates the controller 310 when the absolute value of the voltage equals or exceeds the absolute value of the first threshold.

The controller 310 may be configured to cause the number registered by the counter 320 to increase by one, if, during the time delay, the second voltage comparator 302 determines that the absolute value of the voltage equals or exceeds the absolute value of the second threshold.

The controller 310 may be configured to cause the voltmeter 306 to measure the voltage upon expiration of the time delay. The controller 310 may be configured to connect the electrode to an electrical ground, so as to reset the voltage and discharge any charge carriers accumulated on the electrode. In an embodiment, the electrode is connected to an electrical ground after the expiration of the time delay. In an embodiment, the electrode is connected to an electrical ground for a finite reset time period. The controller 310 may connect the electrode to the electrical ground by controlling the switch 305. The switch may be a transistor such as a field-effect transistor (FET).

In an embodiment, the system 121 has no analog filter network (e.g., a RC network). In an embodiment, the system 121 has no analog circuitry.

The voltmeter 306 may feed the voltage it measures to the controller 310 as an analog or digital signal.

Figure 4:
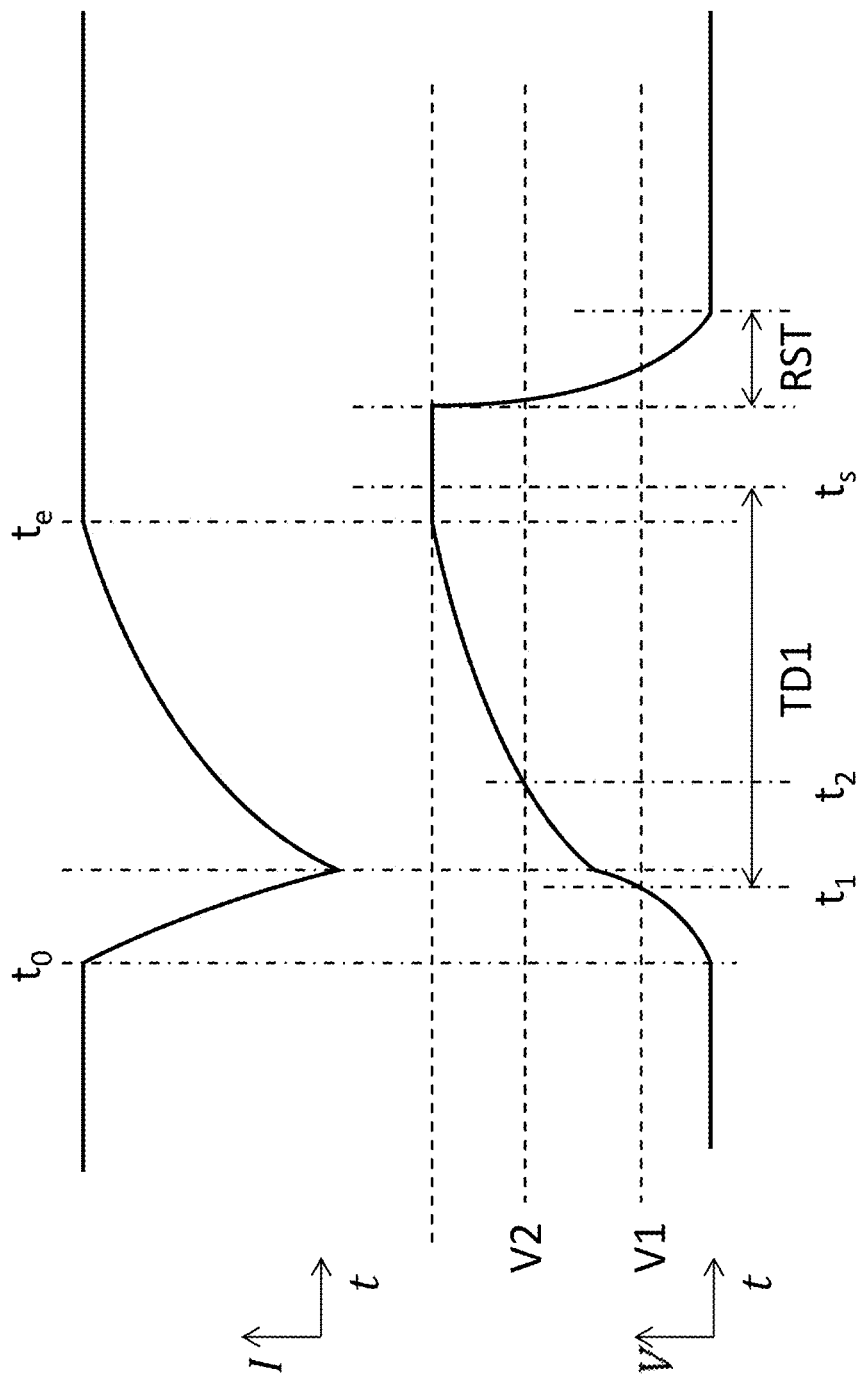
FIG. 4 schematically shows a temporal change of the electric current flowing through an electrode (upper curve) or an electrical contact of a resistor of a radiation absorption layer exposed to radiation, the electric current caused by charge carriers generated by a radiation particle incident on the radiation absorption layer, and a corresponding temporal change of the voltage of the electrode (lower curve), according to an embodiment.

The system 121 may include a capacitor module 309 electrically connected to the electrode or electrical contact of the resistor 300, wherein the capacitor module is configured to collect charge carriers from the electrode. The capacitor module can include a capacitor in the feedback path of an amplifier. The amplifier configured as such is called a capacitive transimpedance amplifier (CTIA). CTIA has high dynamic range by keeping the amplifier from saturating and improves the signal-to-noise ratio by limiting the bandwidth in the signal path. Charge carriers from the electrode accumulate on the capacitor over a period of time ("integration period") (e.g., as shown in FIG. 4, between $t_0$ to $t_1$, or $t_1-t_2$). After the integration period has expired, the capacitor voltage is sampled and then reset by a reset switch. The capacitor module can include a capacitor directly connected to the electrode.

FIG. 4 schematically shows a temporal change of the electric current flowing through the electrode (upper curve) caused by charge carriers generated by a radiation particle incident on the resistor, and a corresponding temporal change of the voltage of the electrode (lower curve). The voltage may be an integral of the electric current with respect to time. At time $t_0$, the radiation particle hits the resistor, charge carriers start being generated in the resistor, electric current starts to flow through the electrode of the resistor, and the absolute value of the voltage of the electrode or electrical contact starts to increase. At time $t_1$, the first voltage comparator 301 determines that the absolute value of the voltage equals or exceeds the absolute value of the first threshold V1, and the controller 310 starts the time delay TD1 and the controller 310 may deactivate the first voltage comparator 301 at the beginning of TD1. If the controller 310 is deactivated before $t_1$, the controller 310 is activated at $t_1$. During TD1, the controller 310 activates the second voltage comparator 302. The term "during" a time delay as used here means the beginning and the expiration (i.e., the end) and any time in between. For example, the controller 310 may activate the second voltage comparator 302 at the expiration of TD1. If during TD1, the second voltage comparator 302 determines that the absolute value of the voltage equals or exceeds the absolute value of the second threshold at time $t_2$, the controller 310 causes the number registered by the counter 320 to increase by one. At time $t_e$, all charge carriers generated by the radiation particle drift out of the radiation absorption layer 110. At time $t_s$, the time delay TD1 expires. In the example of FIG. 4, time $t_s$ is after time $t_e$; namely TD1 expires after all charge carriers generated by the radiation particle drift out of the radiation absorption layer 110. The rate of change of the voltage is thus substantially zero at $t_s$. The controller 310 may be configured to deactivate the second voltage comparator 302 at expiration of TD1 or at $t_2$, or any time in between.

The controller 310 may be configured to cause the voltmeter 306 to measure the voltage upon expiration of the time delay TD1. In an embodiment, the controller 310 causes the voltmeter 306 to measure the voltage after the rate of change of the voltage becomes substantially zero after the expiration of the time delay TD1. The voltage at this moment is proportional to the amount of charge carriers generated by a radiation particle, which relates to the energy of the X-ray photon. The controller 310 may be configured to determine the energy of the radiation particle based on voltage the voltmeter 306 measures. One way to determine the energy is by binning the voltage. The counter 320 may have a sub-counter for each bin. When the controller 310 determines that the energy of the radiation particle falls in a bin, the controller 310 may cause the number registered in the sub-counter for that bin to increase by one. Therefore, the system 121 may be able to detect a radiation image and may be able to resolve energies of each radiation particle.

After TD1 expires, the controller 310 connects the electrode to an electric ground for a reset period RST to allow charge carriers accumulated on the electrode to flow to the ground and reset the voltage. After RST, the system 121 is ready to detect another incident radiation particle. Implicitly, the rate of incident radiation particles the system 121 can handle in the example of FIG. 4 is limited by 1/(TD1+RST). If the first voltage comparator 301 has been deactivated, the controller 310 can activate it at any time before RST expires. If the controller 310 has been deactivated, it may be activated before RST expires.

Figure 5:
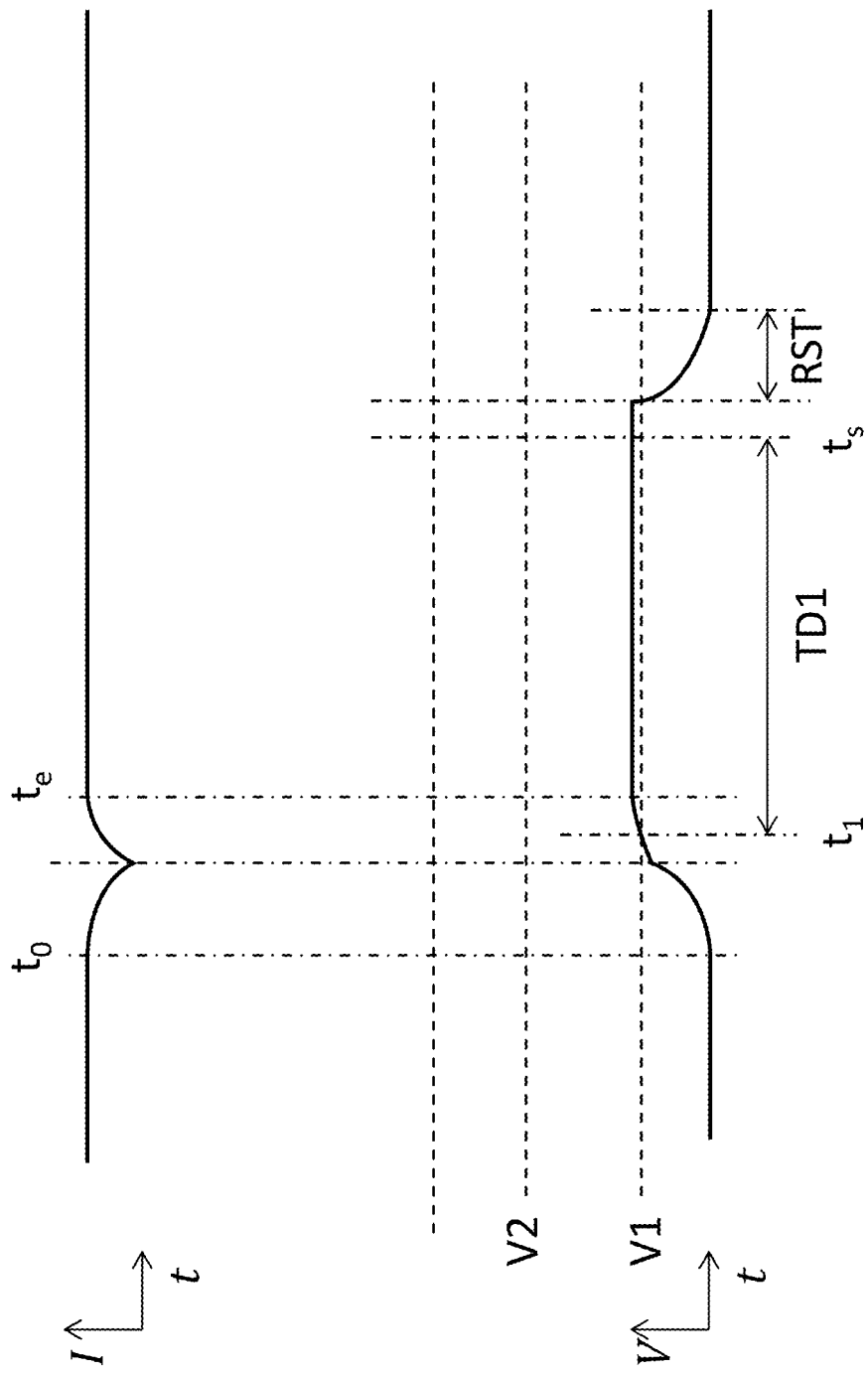
FIG. 5 schematically shows a temporal change of the electric current flowing through the electrode (upper curve) caused by noise (e.g., dark current), and a corresponding temporal change of the voltage of the electrode (lower curve), in the electronics system operating in the way shown in FIG. 4, according to an embodiment.

FIG. 5 schematically shows a temporal change of the electric current flowing through the electrode (upper curve) caused by noise (e.g., dark current, background radiation, scattered radiation, fluorescent X-rays, shared charges from adjacent pixels), and a corresponding temporal change of the voltage of the electrode (lower curve), in the system 121 operating in the way shown in FIG. 4. At time $t_0$, the noise begins. If the noise is not large enough to cause the absolute value of the voltage to exceed the absolute value of V1, the controller 310 does not activate the second voltage comparator 302. If the noise is large enough to cause the absolute value of the voltage to exceed the absolute value of V1 at time $t_1$ as determined by the first voltage comparator 301, the controller 310 starts the time delay TD1 and the controller 310 may deactivate the first voltage comparator 301 at the beginning of TD1. During TD1 (e.g., at expiration of TD1), the controller 310 activates the second voltage comparator 302. The noise is very unlikely large enough to cause the absolute value of the voltage to exceed the absolute value of V2 during TD1. Therefore, the controller 310 does not cause the number registered by the counter 320 to increase. At time $t_e$, the noise ends. At time $t_s$, the time delay TD1 expires. The controller 310 may be configured to deactivate the second voltage comparator 302 at expiration of TD1. The controller 310 may be configured not to cause the voltmeter 306 to measure the voltage if the absolute value of the voltage does not exceed the absolute value of V2 during TD1. After TD1 expires, the controller 310 connects the electrode to an electric ground for a reset period RST to allow charge carriers accumulated on the electrode as a result of the noise to flow to the ground and reset the voltage. Therefore, the system 121 may be very effective in noise rejection.

Figure 6:
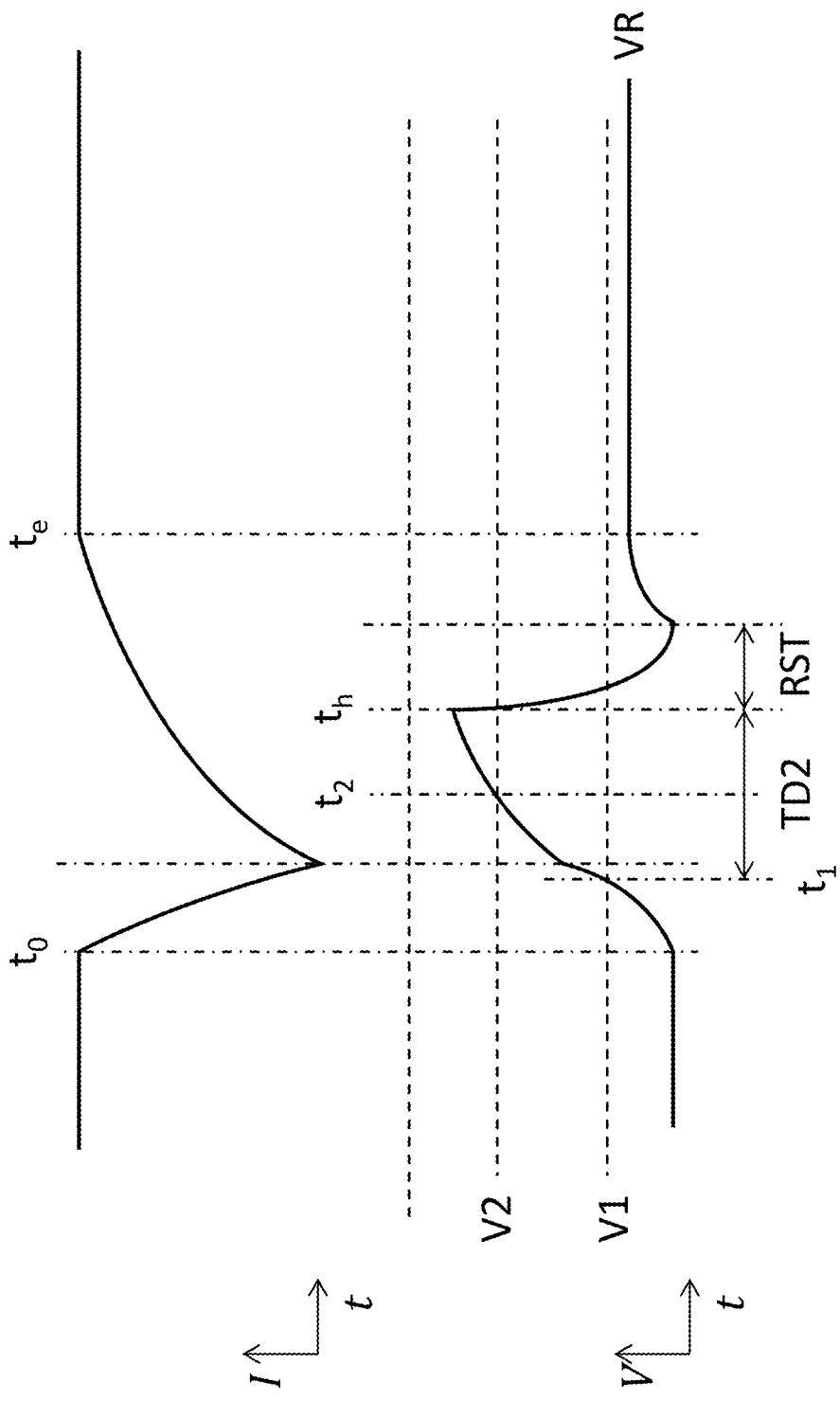
FIG. 6 schematically shows a temporal change of the electric current flowing through an electrode (upper curve) of the radiation absorption layer exposed to radiation, the electric current caused by charge carriers generated by a radiation particle incident on the radiation absorption layer, and a corresponding temporal change of the voltage of the electrode (lower curve), when the electronics system operates to detect incident radiation particles at a higher rate, according to an embodiment.

FIG. 6 schematically shows a temporal change of the electric current flowing through the electrode (upper curve) caused by charge carriers generated by a radiation particle incident on the resistor, and a corresponding temporal change of the voltage of the electrode (lower curve), when the system 121 operates to detect incident radiation particles at a rate higher than 1/(TD1+RST). The voltage may be an integral of the electric current with respect to time. At time $t_0$, the radiation particle hits the resistor, charge carriers start being generated in the resistor, electric current starts to flow through the electrical contact of resistor, and the absolute value of the voltage of the electrode or the electrical contact starts to increase. At time $t_1$, the first voltage comparator 301 determines that the absolute value of the voltage equals or exceeds the absolute value of the first threshold V1, and the controller 310 starts a time delay TD2 shorter than TD1, and the controller 310 may deactivate the first voltage comparator 301 at the beginning of TD2. If the controller 310 is deactivated before $t_1$, the controller 310 is activated at $t_1$. During TD2 (e.g., at expiration of TD2), the controller 310 activates the second voltage comparator 302. If during TD2, the second voltage comparator 302 determines that the absolute value of the voltage equals or exceeds the absolute value of the second threshold at time $t_2$, the controller 310 causes the number registered by the counter 320 to increase by one. At time $t_e$, all charge carriers generated by the radiation particle drift out of the radiation absorption layer 110. At time $t_h$, the time delay TD2 expires. In the example of FIG. 6, time $t_h$ is before time $t_e$; namely TD2 expires before all charge carriers generated by the radiation particle drift out of the radiation absorption layer 110. The rate of change of the voltage is thus substantially non-zero at $t_h$. The controller 310 may be configured to deactivate the second voltage comparator 302 at expiration of TD2 or at $t_2$, or any time in between.

The controller 310 may be configured to extrapolate the voltage at $t_e$ from the voltage as a function of time during TD2 and use the extrapolated voltage to determine the energy of the radiation particle.

After TD2 expires, the controller 310 connects the electrode to an electric ground for a reset period RST to allow charge carriers accumulated on the electrode to flow to the ground and reset the voltage. In an embodiment, RST expires before $t_e$. The rate of change of the voltage after RST may be substantially non-zero because all charge carriers generated by the radiation particle have not drifted out of the radiation absorption layer 110 upon expiration of RST before $t_e$. The rate of change of the voltage becomes substantially zero after $t_e$ and the voltage stabilized to a residue voltage VR after $t_e$. In an embodiment, RST expires at or after $t_e$, and the rate of change of the voltage after RST may be substantially zero because all charge carriers generated by the radiation particle drift out of the radiation absorption layer 110 at $t_e$. After RST, the system 121 is ready to detect another incident radiation particle. If the first voltage comparator 301 has been deactivated, the controller 310 can activate it any time before RST expires. If the controller 310 has been deactivated, it may be activated before RST expires.

Figure 7:
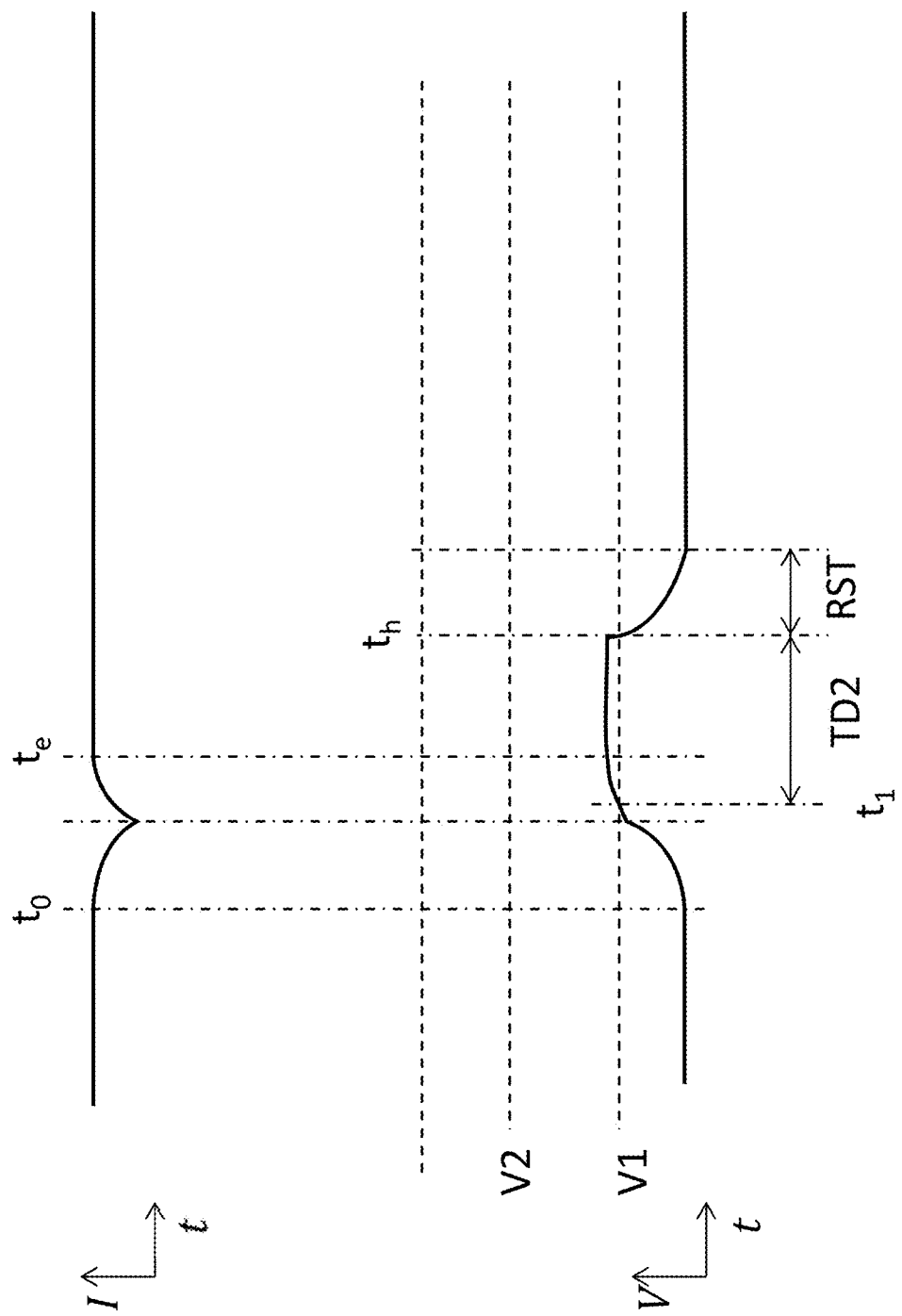
FIG. 7 schematically shows a temporal change of the electric current flowing through the electrode (upper curve) caused by noise (e.g., dark current), and a corresponding temporal change of the voltage of the electrode (lower curve), in the electronics system operating in the way shown in FIG. 6, according to an embodiment.

FIG. 7 schematically shows a temporal change of the electric current flowing through the electrode (upper curve) caused by noise (e.g., dark current, background radiation, scattered radiation, fluorescent X-rays, shared charges from adjacent pixels), and a corresponding temporal change of the voltage of the electrode (lower curve), in the system 121 operating in the way shown in FIG. 6. At time $t_0$, the noise begins. If the noise is not large enough to cause the absolute value of the voltage to exceed the absolute value of V1, the controller 310 does not activate the second voltage comparator 302. If the noise is large enough to cause the absolute value of the voltage to exceed the absolute value of V1 at time $t_1$ as determined by the first voltage comparator 301, the controller 310 starts the time delay TD2 and the controller 310 may deactivate the first voltage comparator 301 at the beginning of TD2. During TD2 (e.g., at expiration of TD2), the controller 310 activates the second voltage comparator 302. The noise is very unlikely large enough to cause the absolute value of the voltage to exceed the absolute value of V2 during TD2. Therefore, the controller 310 does not cause the number registered by the counter 320 to increase. At time $t_e$, the noise ends. At time $t_h$, the time delay TD2 expires. The controller 310 may be configured to deactivate the second voltage comparator 302 at expiration of TD2. After TD2 expires, the controller 310 connects the electrode to an electric ground for a reset period RST to allow charge carriers accumulated on the electrode as a result of the noise to flow to the ground and reset the voltage. Therefore, the system 121 may be very effective in noise rejection.

Figure 8:
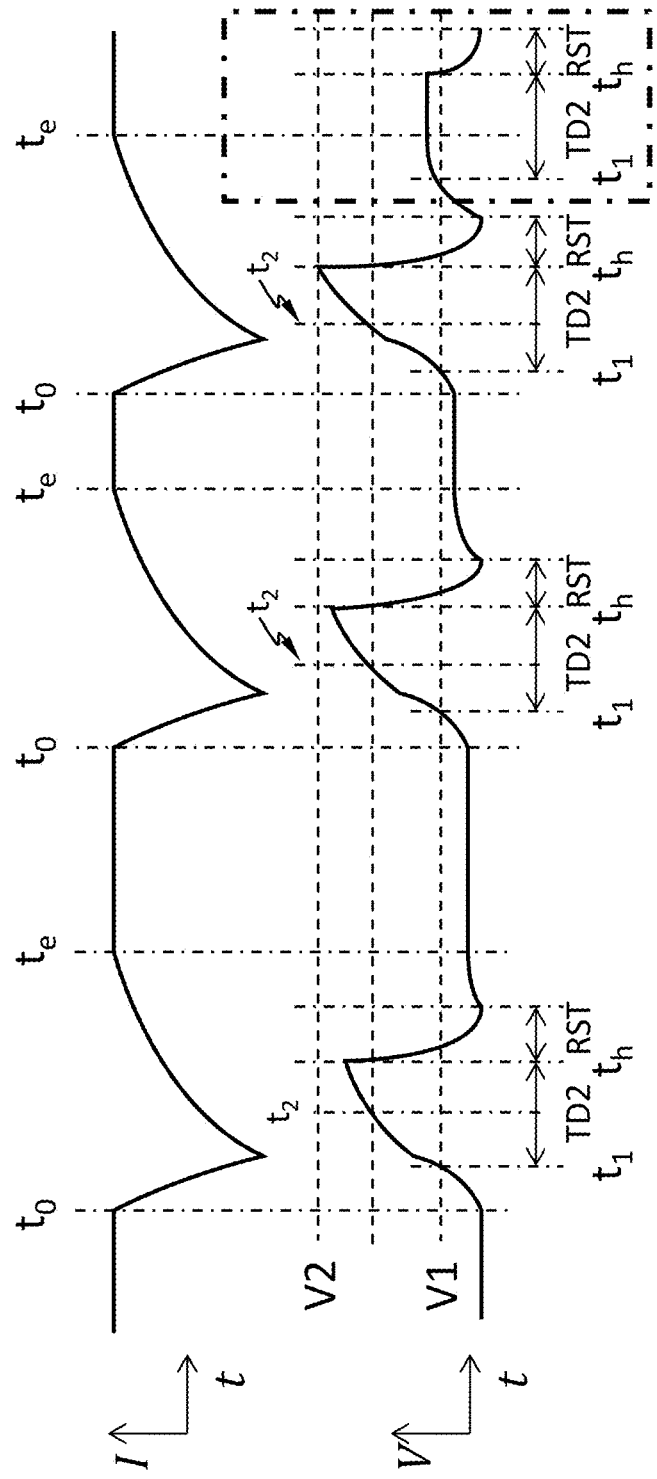
FIG. 8 schematically shows a temporal change of the electric current flowing through the electrode (upper curve) caused by charge carriers generated by a series of radiation particles incident on the radiation absorption layer, and a corresponding temporal change of the voltage of the electrode, in the electronics system operating in the way shown in FIG. 6 with RST expires before $t_e$, according to an embodiment.

FIG. 8 schematically shows a temporal change of the electric current flowing through the electrode (upper curve) caused by charge carriers generated by a series of radiation particles incident on the resistor, and a corresponding temporal change of the voltage of the electrode (lower curve), in the system 121 operating in the way shown in FIG. 6 with RST expires before $t_e$. The voltage curve caused by charge carriers generated by each incident radiation particle is offset by the residue voltage before that radiation particle. The absolute value of the residue voltage successively increases with each incident photon. When the absolute value of the residue voltage exceeds V1 (see the dotted rectangle in FIG. 8), the controller starts the time delay TD2 and the controller 310 may deactivate the first voltage comparator 301 at the beginning of TD2. If no other radiation particle incidence on the resistor during TD2, the controller connects the electrode to the electrical ground during the reset time period RST at the end of TD2, thereby resetting the residue voltage. The residue voltage thus does not cause an increase of the number registered by the counter 320.

Figure 9A:
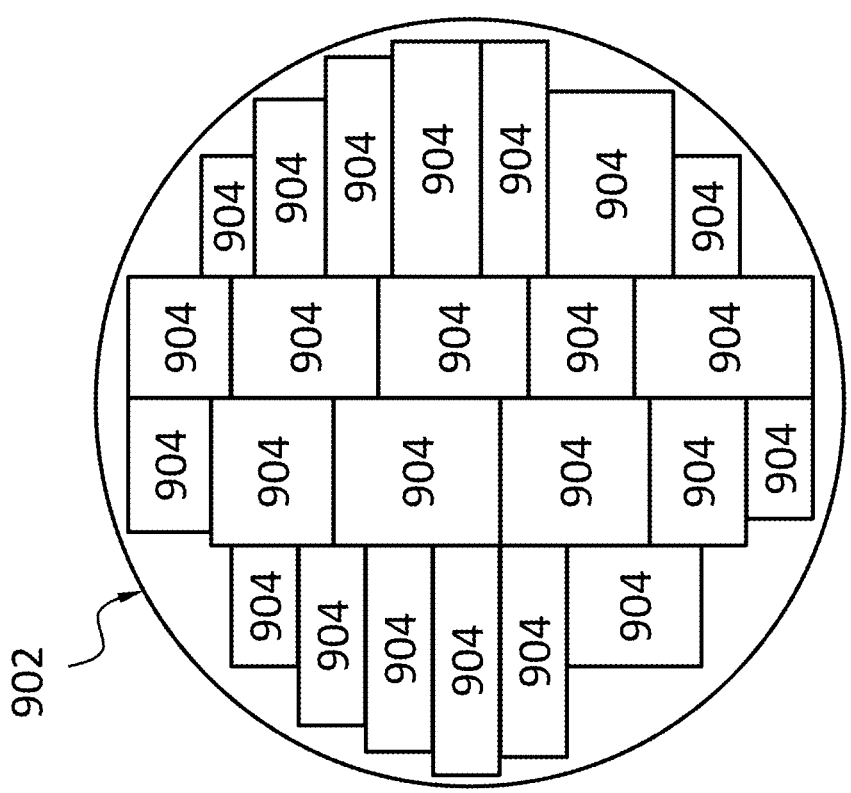
FIG. 9A schematically shows a bottom view of a semiconductor wafer with a plurality of semiconductor single crystal chunks bonded thereon, according to an embodiment.

FIG. 9A schematically shows a bottom view of a semiconductor wafer 902 with a plurality of semiconductor single crystal chunks 904 bonded thereon. The semiconductor single crystal chunks 904 may be cut from one or more manufactured semiconductor single crystals. They may be arranged on the semiconductor wafer 902 and fixed thereon. The arrangement need not have a high precision. The bonding may be by glue, plastic molding, or other known mechanism or techniques to be developed. Although not shown in FIG. 9A, there may be gaps between neighboring single crystal chunks 904 on the semiconductor wafer 902 and the widths of the gaps may not be the same. This bonding of semiconductor single crystals to a wafer may be referred to as wafer reconstruction. In one embodiment, the semiconductor single crystal chunks may be CdZnTe chunks that are suitable to make radiation detectors. For example, the CdZnTe chunks may have size of less than 1 cm, around 1 cm or larger than 1 cm.

The semiconductor single crystal chunks 904 as shown in FIG. 9A are rectangular or square, but in some embodiments, some of the chunks 904 may have various other shapes, such as but not limited to, round, parallelogram, or irregular shapes. In one embodiment, the semiconductor wafer 902 may be conductive. The size of the wafer 902 may be any suitable size, for example, 4 inches, 5 inches, 6 inches, 8 inches, 12 inches, or 18 inches.

Figure 9B:
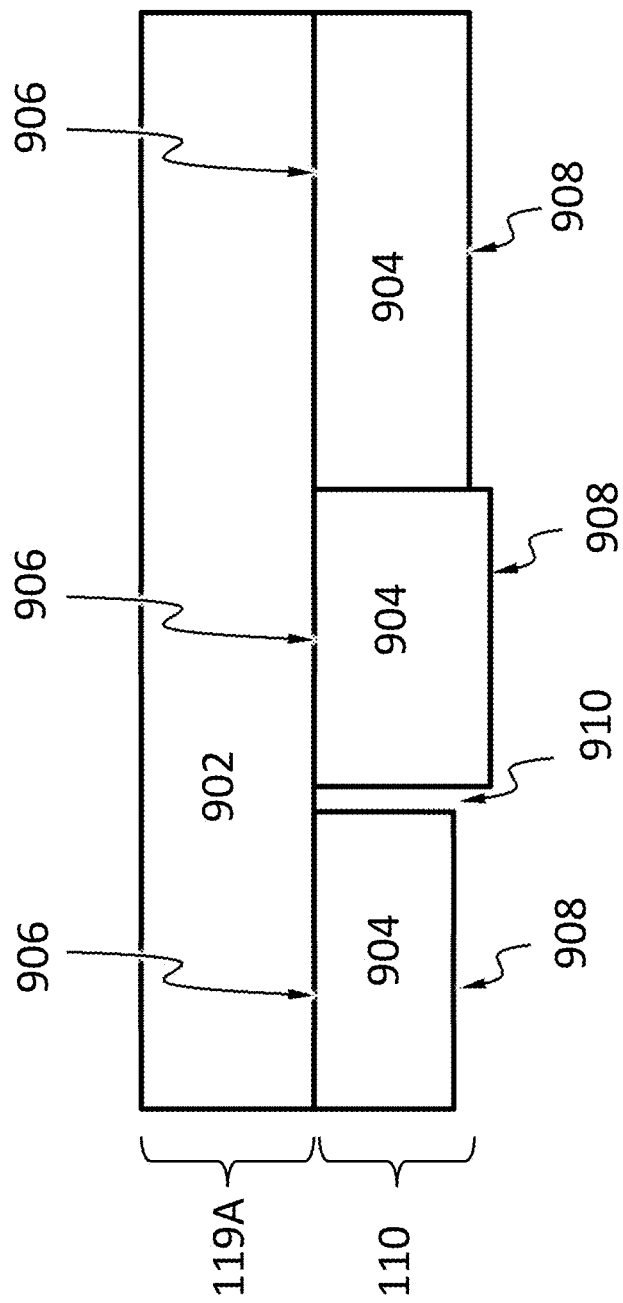
FIG. 9B schematically shows a cross-sectional view of the semiconductor wafer and the plurality of semiconductor single crystal chunks of FIG. 9A, according to an embodiment.

FIG. 9B schematically shows a cross-sectional view of the semiconductor wafer 902 and the plurality of semiconductor single crystal chunks 904 according to one embodiment. As shown in FIG. 9B, each semiconductor single crystal chunks 904 may have a first surface 906 bonded to the semiconductor wafer 902 and a second surface 908 opposite to the first surface 906. A gap 910 is shown in FIG. 9B to illustrate that there may be gaps between neighboring chunks 904. The semiconductor wafer 902 may be conductive and form a common electrode for the plurality of semiconductor single crystal chunks 904, while the plurality of semiconductor single crystal chunks 904 may for a radiation absorption layer 110. That is, the semiconductor wafer 902 may be an embodiment of the electrical contact 119A shown in FIG. 1B. In one embodiment, the semiconductor single crystal chunks 904 may have a thickness of around 1 to 2 mm before being polished. As shown in FIG. 9B, the semiconductor single crystal chunks 904 may have different thicknesses.

FIG. 10A schematically shows a semiconductor wafer 902 with a plurality of semiconductor single crystal chunks 904 bonded thereon, according to an embodiment. The plurality of semiconductor single crystal chunks 904 may have the same thickness. In one embodiment, the same thickness of the plurality of semiconductor single crystal chunks 904 may be obtained by polishing after they have been bonded on the semiconductor wafer 902.

Figure 10B:
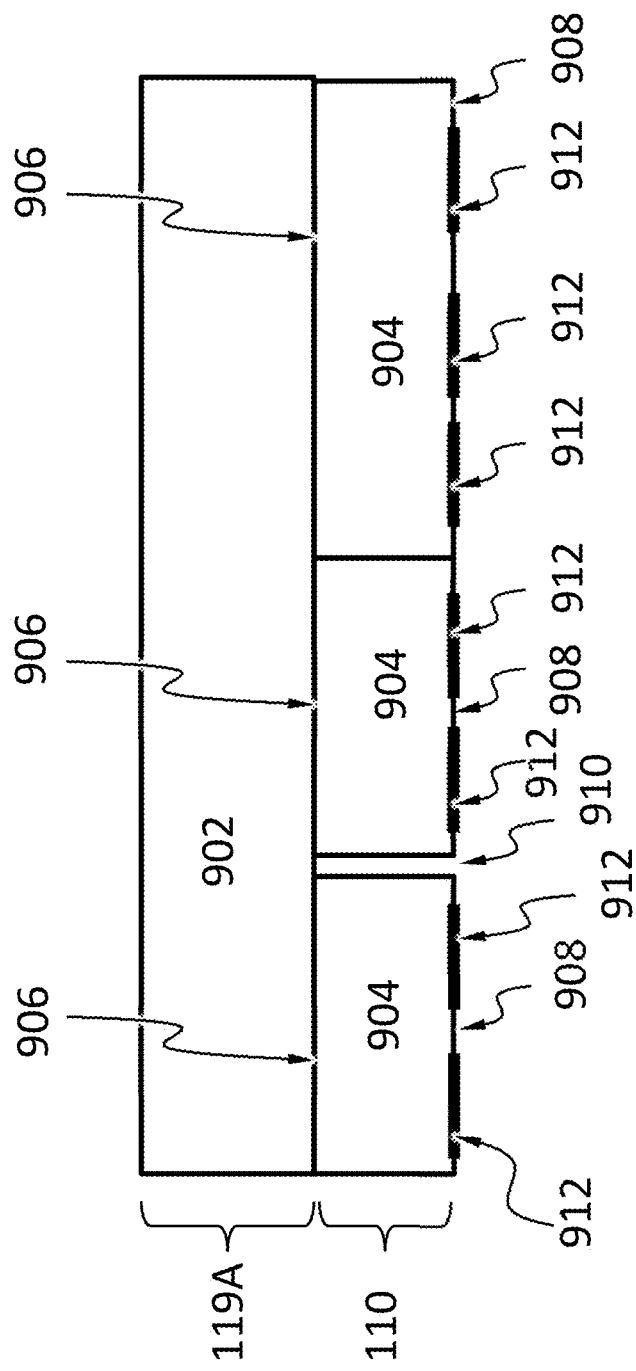
FIG. 10B schematically shows electrodes on the plurality of semiconductor single crystal chunks of FIG. 10A, according to an embodiment.

FIG. 10B schematically shows electrodes 912 on the plurality of semiconductor single crystal chunks 904 of FIG. 10A, according to an embodiment. Each of the chunks 904 may have a plurality of electrodes 912. The electrodes 912 may be obtained using semiconductor wafer processes. For example, the electrodes 912 may be generated using known or yet to be developed semiconductor wafer processes. Each chunk 904 may have a plurality of electrodes, for example, hundreds or thousands of electrodes. In one embodiment, each chunk 904 may have about 5000 electrodes.

FIG. 10C schematically shows pillars 914 deposited on the plurality of semiconductor single crystal chunks 904. In one embodiment, the pillars 914 may be conductive, for example, made of copper. The pillars 914 may be deposited using semiconductor wafer processes. For example, the pillars 914 may be obtained using known or to be developed semiconductor wafer processes.

Figure 10D:
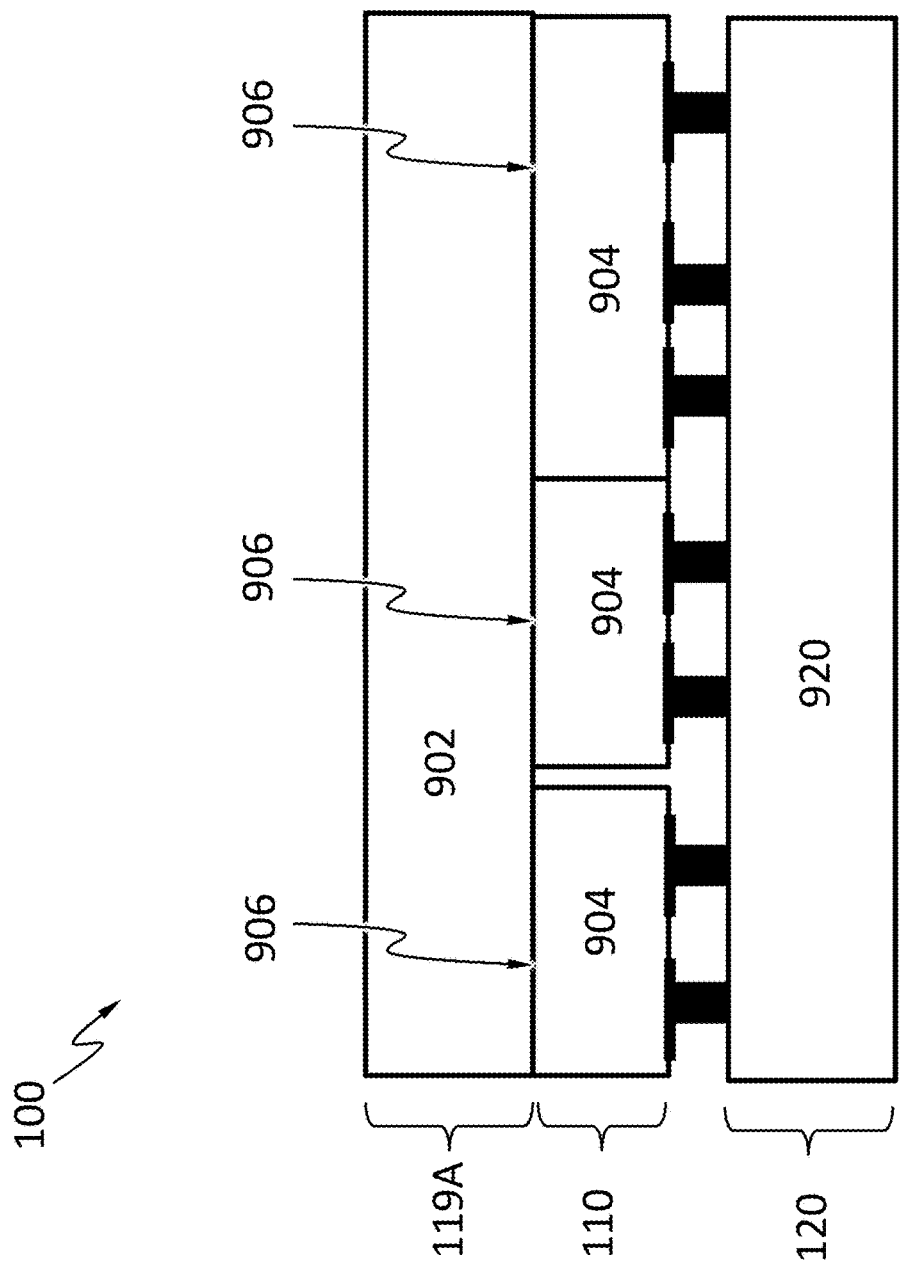
FIG. 10D schematically shows the plurality of semiconductor single crystal chunks of FIG. 10C being bonded to a semiconductor wafer, according to an embodiment.

FIG. 10D schematically shows that the plurality of semiconductor single crystal chunks 904 may be bonded to a second semiconductor wafer 920 by the pillars 914, according to an embodiment. Compared to FIG. 10C, the reference numerals 908 for the second surface, 910 for the gap, 912 for the electrodes and 914 for the pillars are omitted on FIG. 10D to reduce clutter. The semiconductor wafer 920 may comprise the electronics layer 120 as described herein. In one embodiment, the semiconductor wafer 920 may comprise a plurality of ASIC to read out and process the signals from the plurality of semiconductor single crystal chunks. In one embodiment, the bonding may be a wafer level bonding and performed using room temperature bonding. The final product of the processes 9A-9B and 10A-10D may be used as one radiation detector 100 or may be cut into smaller modules such that each smaller module may be used as a radiation detector 100.

Figure 11:
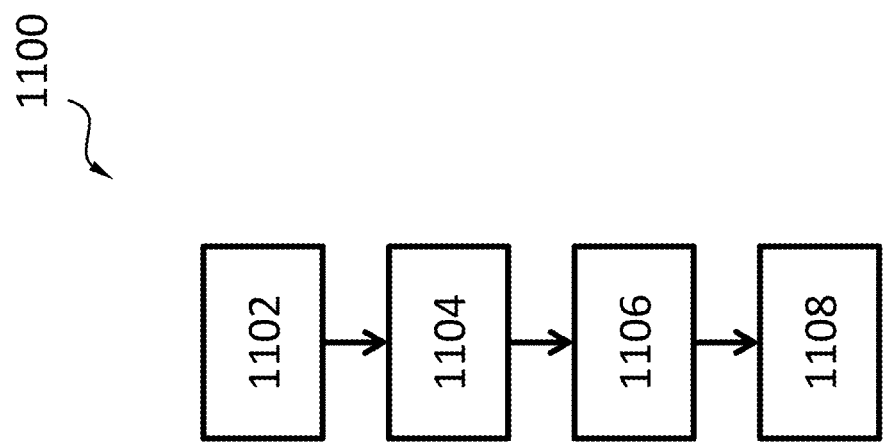
FIG. 11 shows a flow chart of a process of making a semiconductor detector, according to an embodiment.

FIG. 11 shows a flow chart of a process 1100 of making a semiconductor radiation detector (e.g., detector 100) as described herein. According to one embodiment, the process 1100 may start at block 1102, in which a plurality of semiconductor single crystal chunks (e.g., chunks 904) may be obtained. Each of the plurality of semiconductor single crystal chunk may have a first surface and a second surface, and the second surface may be on an opposite side to the first surface. At block 1104, the plurality of semiconductor single crystal chunks may be bonded to a first semiconductor wafer (e.g., wafer 902) by respective first surfaces. At block 1106, a plurality of electrodes (e.g., electrodes 912) may be formed on respective second surfaces of each of the plurality of semiconductor single crystal chunks. At block 1108, pillars (e.g., pillars 914) may be deposited on each of the plurality of semiconductor single crystal chunks for bonding to a second semiconductor wafer (e.g., wafer 920). In one embodiment, the semiconductor single crystal chunks may be CdZnTe chunks.

FIGS. 12-18 schematically show various systems each comprising an image sensor 9000. The image sensor 9000 may be an embodiment of an image sensor comprising one or more semiconductor radiation detectors described herein. It should be noted a radiation detector according to an embodiment may be used to detect one or more types of radiation and X-ray is just one example. For example, the radiation may be an electromagnetic radiation such as infrared light, visible light, ultraviolet light, X-ray or γ-ray. The radiation may be of other types such as charged and non-charged particles as described herein.

Figure 12:
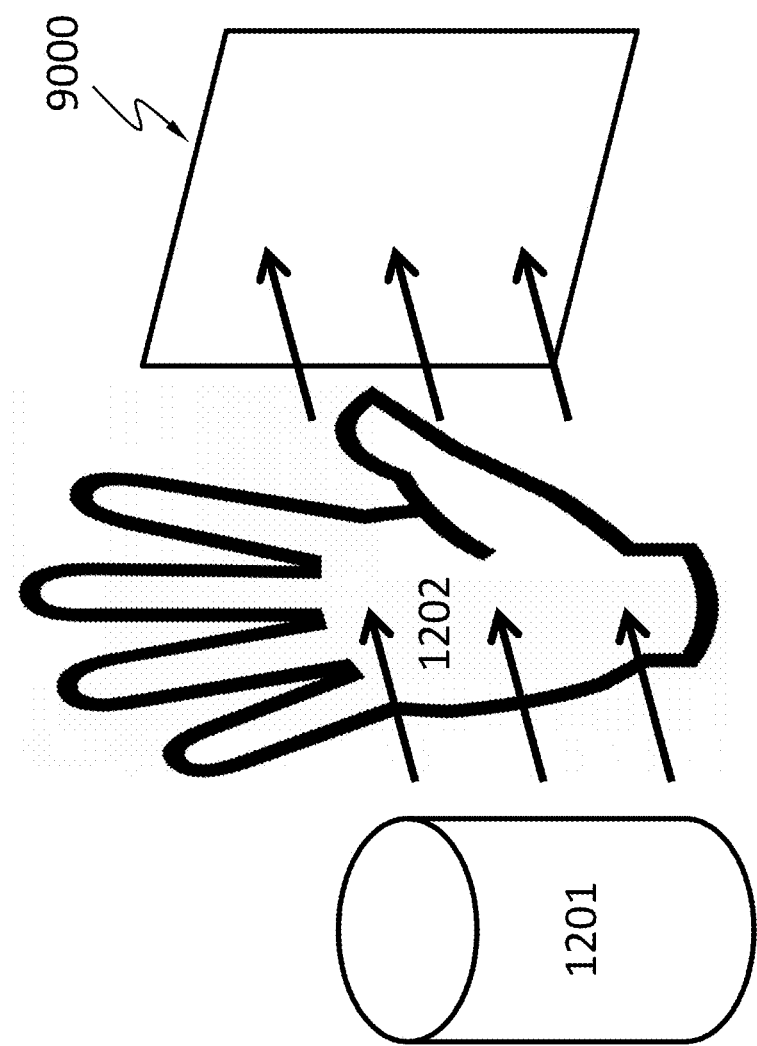
FIG. 12 schematically shows a system comprising the radiation detector described herein, suitable for medical imaging such as chest radiation radiography, abdominal radiation radiography, etc., according to an embodiment FIG. 13 schematically shows a system comprising the semiconductor radiation detector described herein suitable for dental radiography, according to an embodiment.

FIG. 12 schematically shows a system comprising the image sensor 9000 described herein. The system may be used for medical imaging such as chest X-ray radiography, abdominal X-ray radiography, etc. The system comprises an X-ray source 1201. X-ray emitted from the X-ray source 1201 penetrates an object 1202 (e.g., a human body part such as chest, limb, abdomen), is attenuated by different degrees by the internal structures of the object 1202 (e.g., bones, muscle, fat and organs, etc.), and is projected to the image sensor 9000. The image sensor 9000 forms an image by detecting the intensity distribution of the X-ray.

Figure 13:
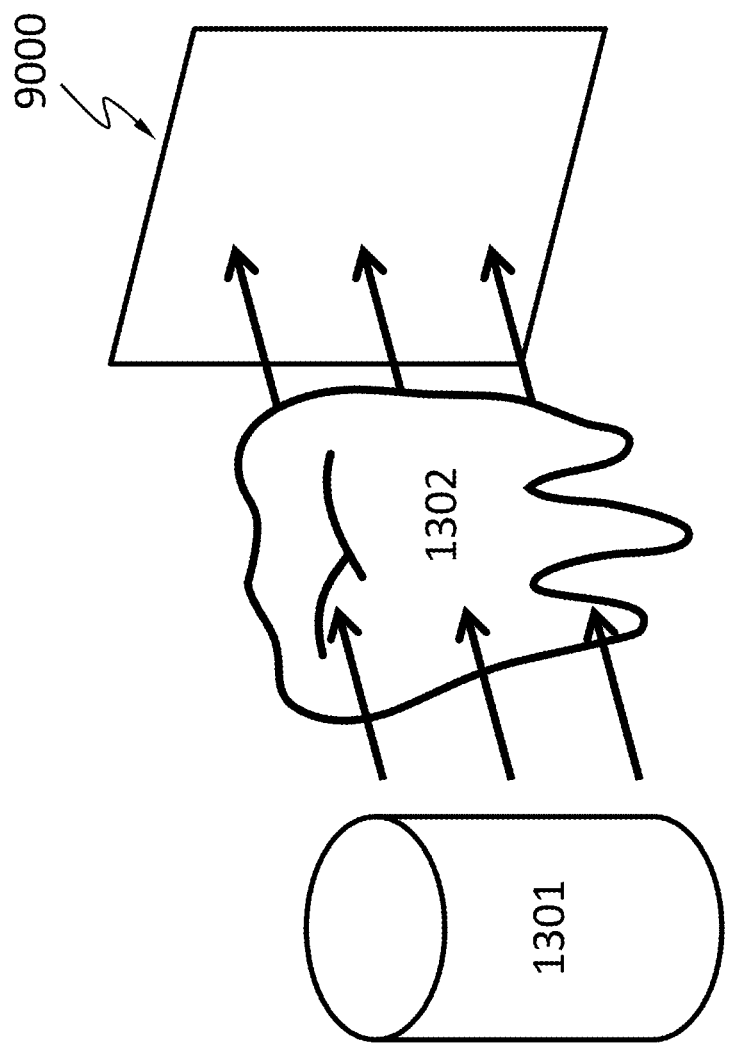

FIG. 13 schematically shows a system comprising the image sensor 9000 described herein. The system may be used for medical imaging such as dental X-ray radiography. The system comprises an X-ray source 1301. X-ray emitted from the X-ray source 1301 penetrates an object 1302 that is part of a mammal (e.g., human) mouth. The object 1302 may include a maxilla bone, a palate bone, a tooth, the mandible, or the tongue. The X-ray is attenuated by different degrees by the different structures of the object 1302 and is projected to the image sensor 9000. The image sensor 9000 forms an image by detecting the intensity distribution of the X-ray. Teeth absorb X-ray more than dental caries, infections, periodontal ligament. The dosage of X-ray radiation received by a dental patient is typically small (around 0.150 mSv for a full mouth series).

Figure 14:
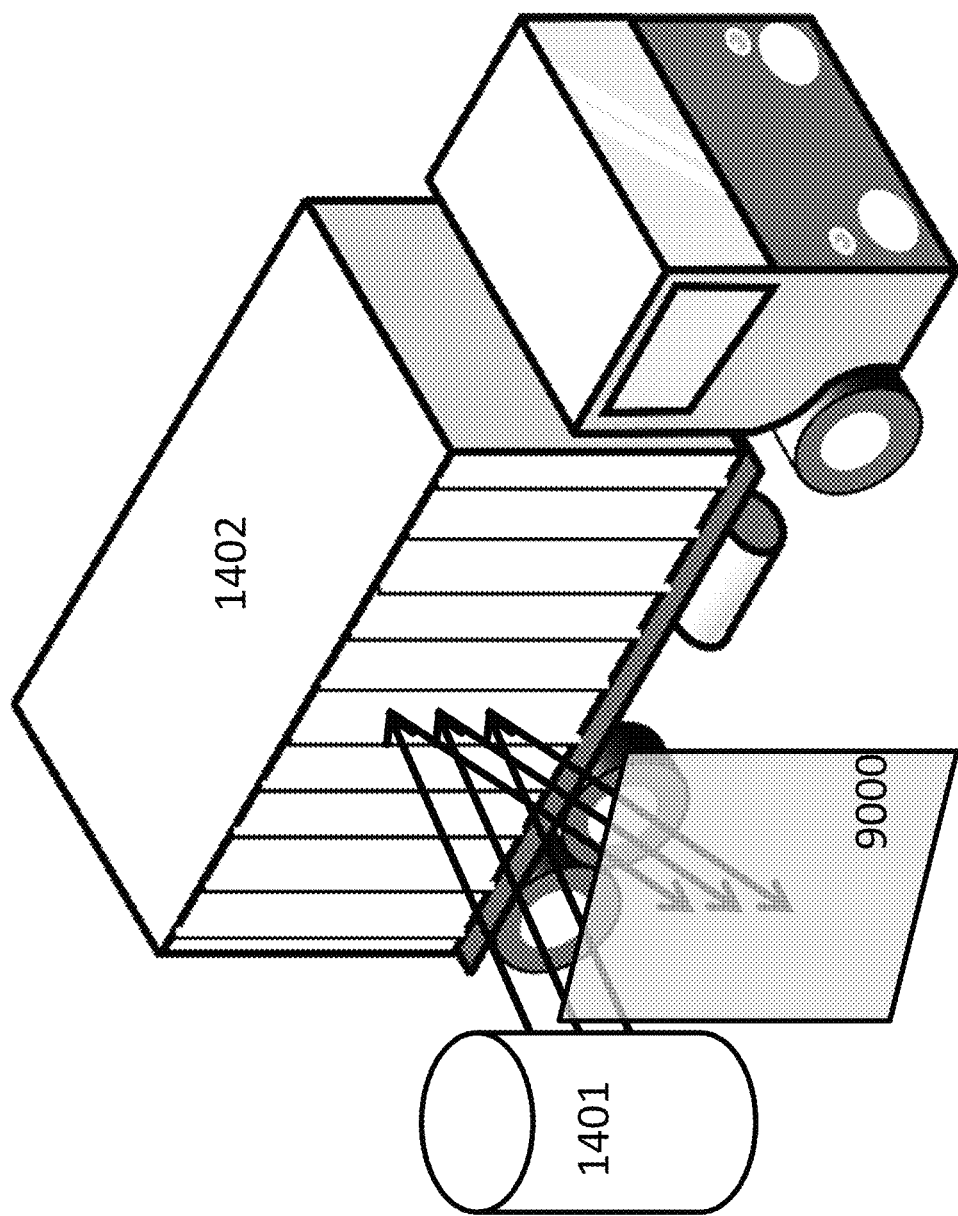
FIG. 14 schematically shows a cargo scanning or non-intrusive inspection (NII) system comprising the radiation detector described herein, according to an embodiment.

FIG. 14 schematically shows a cargo scanning or non-intrusive inspection (NII) system comprising the image sensor 9000 described herein. The system may be used for inspecting and identifying goods in transportation systems such as shipping containers, vehicles, ships, luggage, etc. The system comprises an X-ray source 1401. X-ray emitted from the X-ray source 1401 may backscatter from an object 1402 (e.g., shipping containers, vehicles, ships, etc.) and be projected to the image sensor 9000. Different internal structures of the object 1402 may backscatter X-ray differently. The image sensor 9000 forms an image by detecting the intensity distribution of the backscattered X-ray and/or energies of the backscattered X-ray photons.

Figure 15:
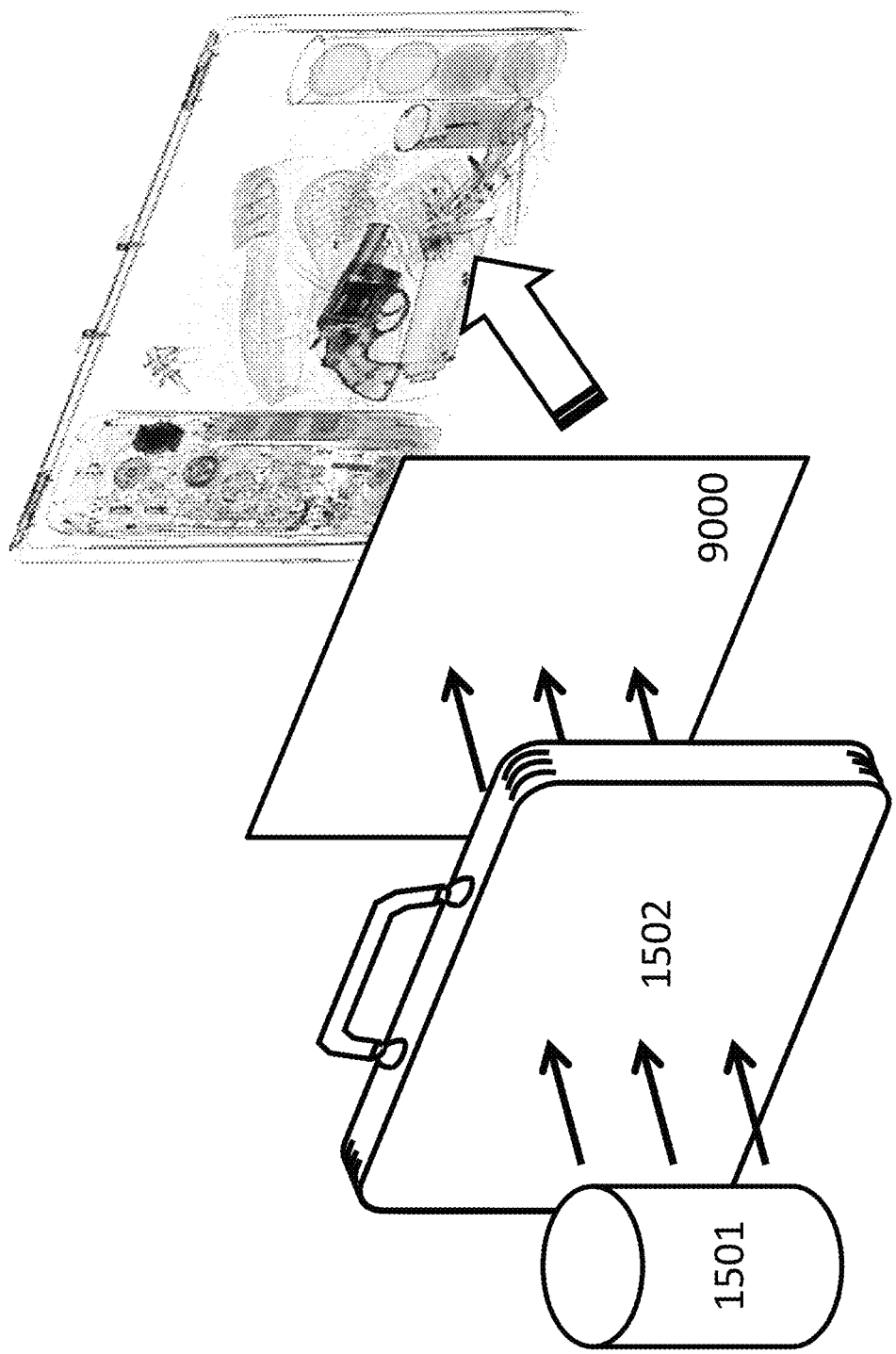
FIG. 15 schematically shows another cargo scanning or non-intrusive inspection (NII) system comprising the radiation detector described herein, according to an embodiment.

FIG. 15 schematically shows another cargo scanning or non-intrusive inspection (NII) system comprising the image sensor 9000 described herein. The system may be used for luggage screening at public transportation stations and airports. The system comprises an X-ray source 1501. X-ray emitted from the X-ray source 1501 may penetrate a piece of luggage 1502, be differently attenuated by the contents of the luggage, and projected to the image sensor 9000. The image sensor 9000 forms an image by detecting the intensity distribution of the transmitted X-ray. The system may reveal contents of luggage and identify items forbidden on public transportation, such as firearms, narcotics, edged weapons, flammables.

Figure 16:
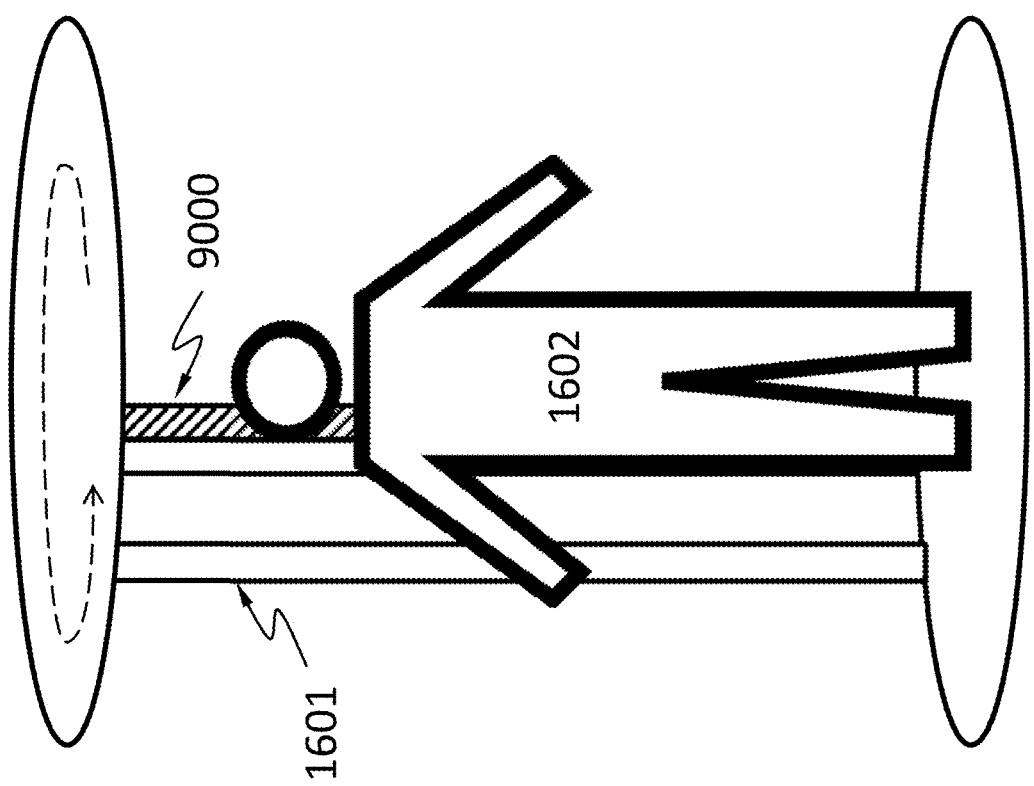
FIG. 16 schematically shows a full-body scanner system comprising the radiation detector described herein, according to an embodiment.

FIG. 16 schematically shows a full-body scanner system comprising the image sensor 9000 described herein. The full-body scanner system may detect objects on a person's body for security screening purposes, without physically removing clothes or making physical contact. The full-body scanner system may be able to detect non-metal objects. The full-body scanner system comprises an X-ray source 1601. X-ray emitted from the X-ray source 1601 may backscatter from a human 1602 being screened and objects thereon, and be projected to the image sensor 9000. The objects and the human body may backscatter X-ray differently. The image sensor 9000 forms an image by detecting the intensity distribution of the backscattered X-ray. The image sensor 9000 and the X-ray source 1601 may be configured to scan the human in a linear or rotational direction.

Figure 17:
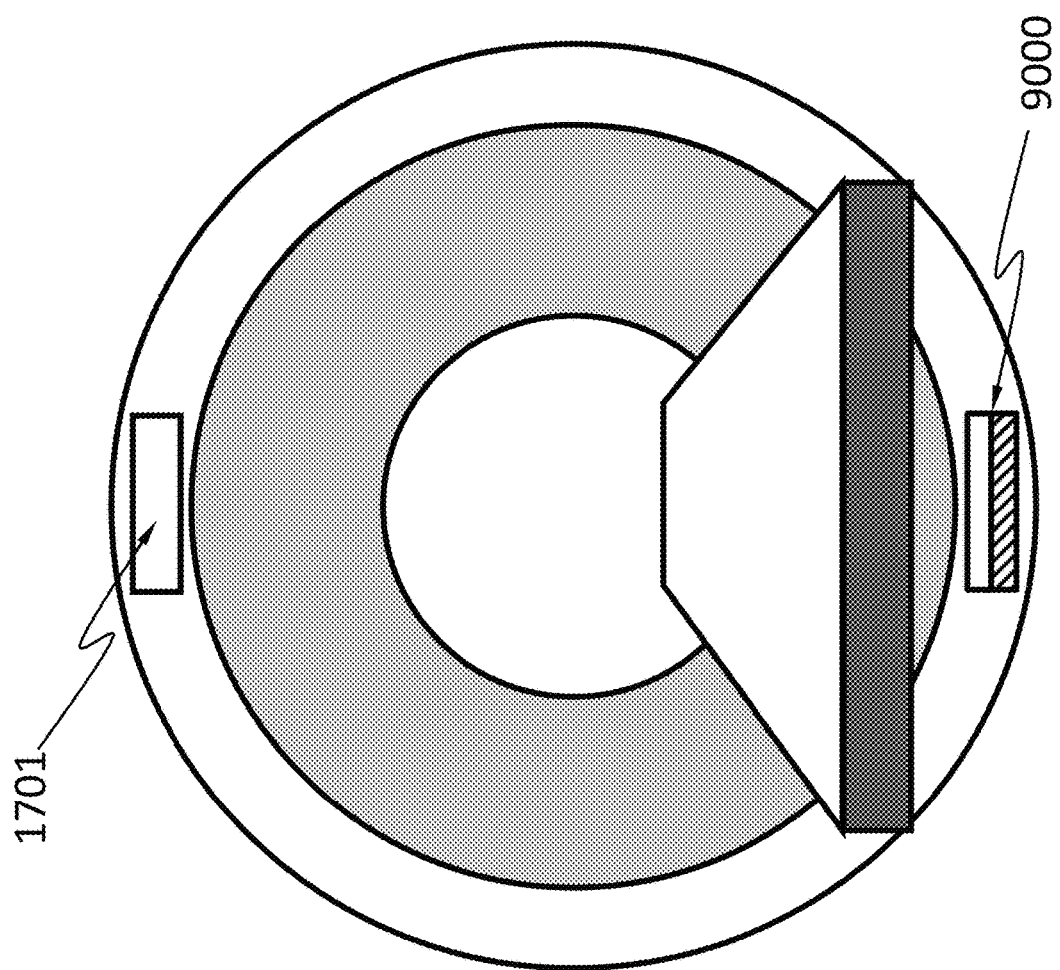
FIG. 17 schematically shows a computed tomography (CT) system comprising the radiation detector described herein, according to an embodiment.

FIG. 17 schematically shows an X-ray computed tomography (X-ray CT) system. The X-ray CT system uses computer-processed X-rays to produce tomographic images (virtual "slices") of specific areas of a scanned object. The tomographic images may be used for diagnostic and therapeutic purposes in various medical disciplines, or for flaw detection, failure analysis, metrology, assembly analysis and reverse engineering. The X-ray CT system comprises the image sensor 9000 described herein and an X-ray source 1701. The image sensor 9000 and the X-ray source 1701 may be configured to rotate synchronously along one or more circular or spiral paths.

Figure 18:
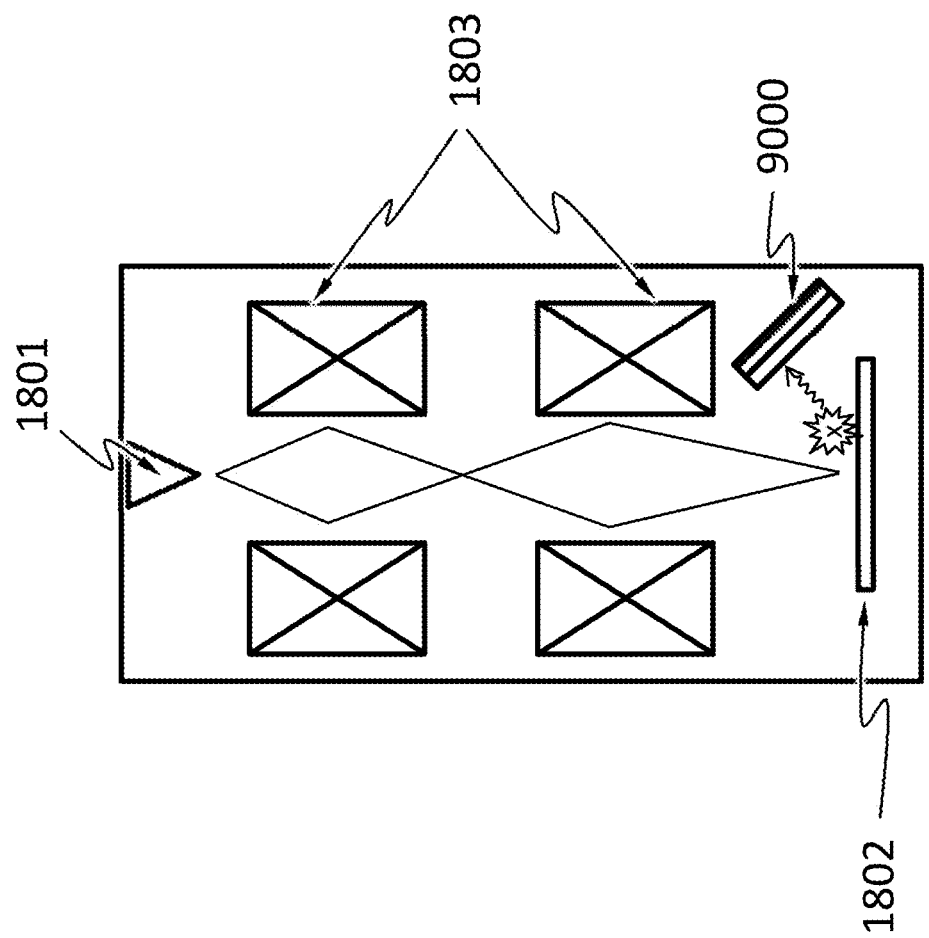
FIG. 18 schematically shows an electron microscope comprising the radiation detector described herein, according to an embodiment.

FIG. 18 schematically shows an electron microscope. The electron microscope comprises an electron source 1801 (also called an electron gun) that is configured to emit electrons. The electron source 1801 may have various emission mechanisms such as thermionic, photocathode, cold emission, or plasmas source. The emitted electrons pass through an electronic optical system 1803, which may be configured to shape, accelerate, or focus the electrons. The electrons then reach a sample 1802 and an image detector may form an image therefrom. The electron microscope may comprise the image sensor 9000 described herein, for performing energy-dispersive X-ray spectroscopy (EDS). EDS is an analytical technique used for the elemental analysis or chemical characterization of a sample. When the electrons incident on a sample, they cause emission of characteristic X-rays from the sample. The incident electrons may excite an electron in an inner shell of an atom in the sample, ejecting it from the shell while creating an electron hole where the electron was. An electron from an outer, higher-energy shell then fills the hole, and the difference in energy between the higher-energy shell and the lower energy shell may be released in the form of an X-ray. The number and energy of the X-rays emitted from the sample can be measured by the image sensor 9000.

The image sensor 9000 described here may have other applications such as in an X-ray telescope, X-ray mammography, industrial X-ray defect detection, X-ray microscopy or microradiography, X-ray casting inspection, X-ray non-destructive testing, X-ray weld inspection, X-ray digital subtraction angiography, etc. It may be suitable to use this image sensor 9000 in place of a photographic plate, a photographic film, a PSP plate, an X-ray image intensifier, a scintillator, or another semiconductor X-ray detector.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method for making an apparatus suitable for detecting radiation, the method comprising:
    obtaining a plurality of semiconductor single crystal chunks each having a first surface and a second surface, the second surface being opposite to the first surface;
    bonding the plurality of semiconductor single crystal chunks by respective first surfaces to a first semiconductor wafer, the plurality of semiconductor single crystal chunks forming a radiation absorption layer;
    forming a plurality of electrodes on respective second surfaces of each of the plurality of semiconductor single crystal chunks;
    depositing pillars on each of the plurality of semiconductor single crystal chunks; and
    bonding the plurality of semiconductor single crystal chunks to a second semiconductor wafer by the pillars.

2. The method of claim 1, wherein the plurality of semiconductor single crystal chunks are cadmium zinc telluride (CdZnTe) chunks.

3. The method of claim 1, wherein the plurality of semiconductor single crystal chunks are bonded to the first semiconductor wafer by glue or plastic molding.

4. The method of claim 1, wherein the first semiconductor wafer is conductive and serve as a common electrode for the plurality of semiconductor single crystals chunks.

5. The method of claim 1, wherein the plurality of electrodes on the plurality of semiconductor single crystal chunks are formed by semiconductor wafer processes.

6. The method of claim 1, wherein the pillars are conductive pillar bumps.

7. The method of claim 6, wherein the pillars are deposited using semiconductor wafer processes.

8. The method of claim 1, further comprising polishing the second surfaces of the plurality of semiconductor single crystal chunks so that the plurality of semiconductor single crystal chunks are of the same thickness.

9. The method of claim 1, wherein the first semiconductor wafer forms a common electrode for the plurality of semiconductor single crystal chunks.

10. The method of claim 9, wherein the plurality of semiconductor single crystal chunks form resistors between the common electrode at the first surfaces and the plurality of electrodes on the second surfaces.

11. The method of claim 1, wherein the radiation absorption layer is configured to detect one of electromagnetic radiation including ultraviolet (UV), X-ray, gamma ray.

12. The method of claim 1, wherein the radiation absorption layer is configured to detect one of particle radiation including alpha particles, beta particles and neutron particles.

13. The method of claim 1, wherein bonding of the plurality of semiconductor single crystal chunks to the second semiconductor wafer is performed by wafer level room temperature bonding.

14. The method of claim 1, wherein the second semiconductor wafer comprises an electronics layer for processing signals generated in the radiation absorption layer.

15. The method of claim 14, wherein the electronics layer comprises an electronics system connected to one of the plurality of electrodes of the plurality of semiconductor single crystal chunks, the electronics system comprises:
    a first voltage comparator configured to compare a voltage of at least one of the electrodes to a first threshold;
    a second voltage comparator configured to compare the voltage to a second threshold;
    a counter configured to register a number of radiation photons or particles reaching the radiation absorption layer;
    a controller;
    wherein the controller is configured to start a time delay from a time at which the first voltage comparator determines that an absolute value of the voltage equals or exceeds an absolute value of the first threshold;
    wherein the controller is configured to activate the second voltage comparator during the time delay;
    wherein the controller is configured to cause the number registered by the counter to increase by one, if the second voltage comparator determines that an absolute value of the voltage equals or exceeds an absolute value of the second threshold.

16. The method of claim 15, wherein the electronics system further comprises a capacitor module electrically connected to the electrode, wherein the capacitor module is configured to collect charge carriers from the electrode.

17. The method of claim 15, wherein the controller is configured to activate the second voltage comparator at a beginning or expiration of the time delay.

18. The method of claim 15, wherein the electronics system further comprises a voltmeter, wherein the controller is configured to cause the voltmeter to measure the voltage upon expiration of the time delay.

19. The method of claim 15, wherein the controller is configured to determine a radiation particle energy based on a value of the voltage measured upon expiration of the time delay.

20. The method of claim 15, wherein the controller is configured to connect the electrode to an electrical ground.

21. The method of claim 15, wherein a rate of change of the voltage is substantially zero at expiration of the time delay.

22. The method of claim 15, wherein a rate of change of the voltage is substantially non-zero at expiration of the time delay.

* * * * *